United States Patent [19]
Thurston et al.

[11] Patent Number: 5,392,776
[45] Date of Patent: Feb. 28, 1995

[54] METHOD AND APPARATUS FOR DETECTING CATARACTOGENESIS

[75] Inventors: George M. Thurston, Belmont; Douglas L. Hayden, Cambridge; Victor G. Taratuta, Boston; Joyce A. Peetermans, Newton; George B. Benedek, Belmont, all of Mass.

[73] Assignee: Oculon Corporation, Cambridge, Mass.

[21] Appl. No.: 948,273

[22] Filed: Sep. 21, 1992

[51] Int. Cl.$^6$ .............................................. A61B 3/10
[52] U.S. Cl. ............................ 128/633; 128/653.001; 128/745
[58] Field of Search ............... 128/633, 664, 665, 666, 128/715; 351/205, 213, 201

[56] References Cited

U.S. PATENT DOCUMENTS

| | | | |
|---|---|---|---|
| 4,702,576 | 10/1987 | Magnante | 351/214 |
| 4,957,113 | 9/1990 | Benedek | 128/665 |
| 5,072,731 | 12/1991 | Taratuta et al. | 128/633 |
| 5,258,788 | 11/1993 | Furuya | 128/633 |
| 5,279,296 | 1/1994 | Thurston et al. | 128/633 |

FOREIGN PATENT DOCUMENTS

| | | | |
|---|---|---|---|
| 2112171A | 7/1983 | United Kingdom | A61B 3/10 |
| WO92/11799 | 7/1992 | WIPO | A61B 3/117 |

Primary Examiner—Angela D. Sykes
Assistant Examiner—Robert L. Nasser
Attorney, Agent, or Firm—Seed and Berry

[57] ABSTRACT

A method and apparatus for detecting cataractogenesis is disclosed. Quasielastic light scattering data are collected from the lens of an individual to be tested for cataractogenesis. The data are collected from specific and reproducible sites within the lens by means of measurements made using a reticle in the apparatus and processed by an autocorrelator. The data from the autocorrelator are then fit to a double exponential form of autocorrelation function and the resulting functional form is transformed to produce at least one dimensionless parameter $F_{mos}$. This parameter has been found to change predictably with the individual's age and, accordingly, is useful in detecting and determining the degree of cataractogenesis in the individual.

56 Claims, 13 Drawing Sheets

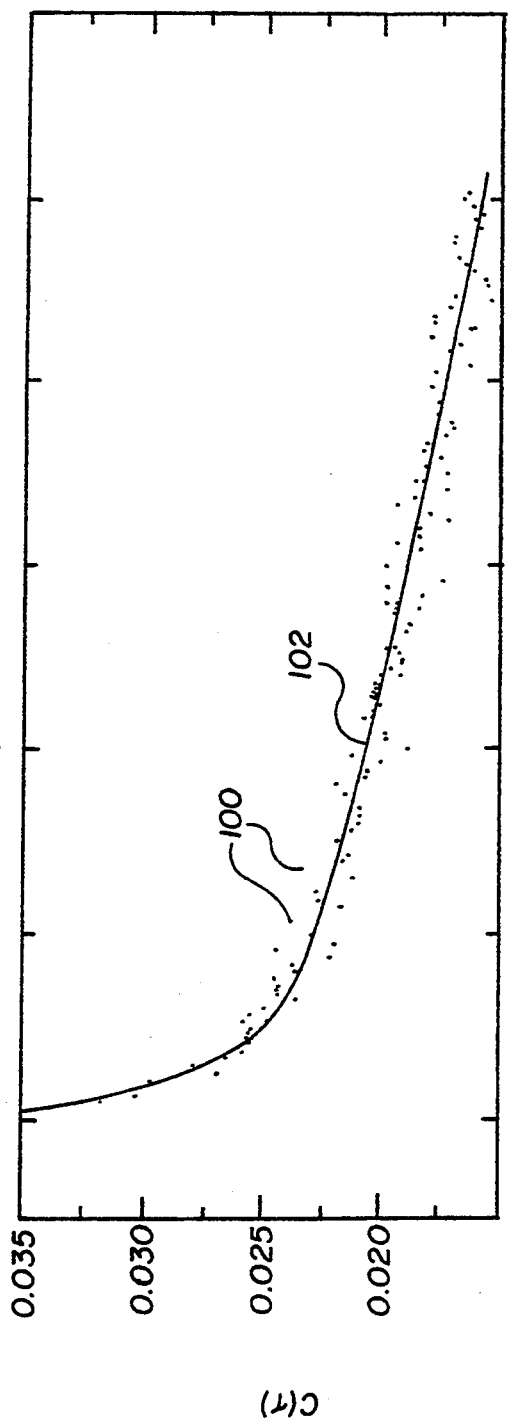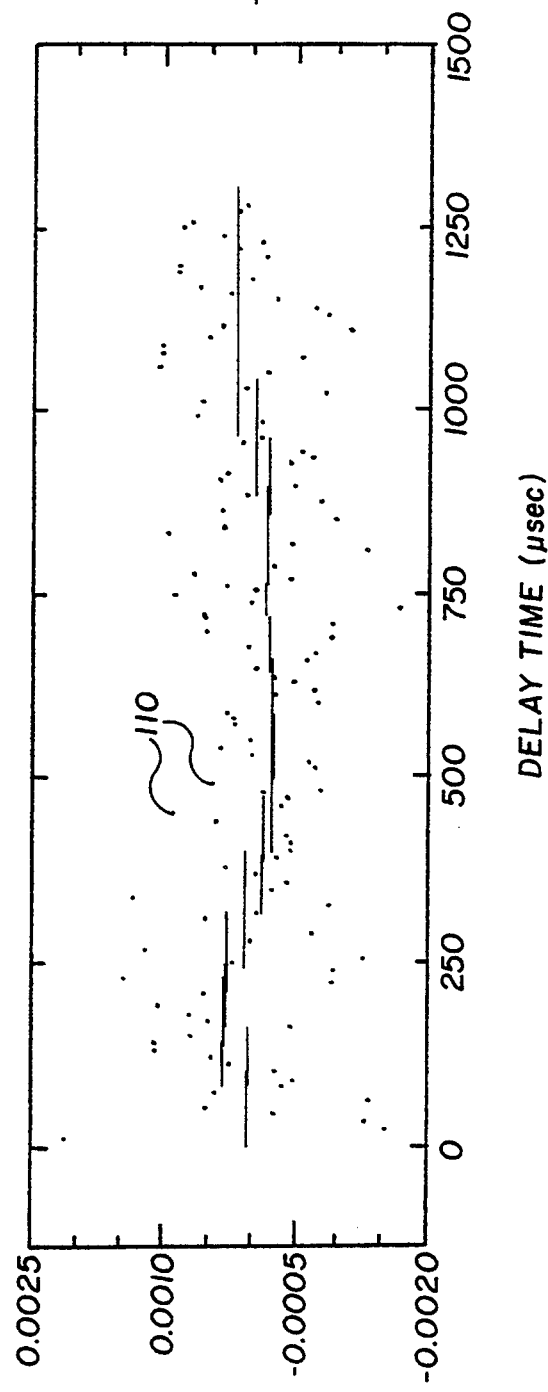

FIG. 5C

FIT 128 POINTS WITH 'ocu.5'
INSTRUMENTAL WIGHTS
CONVERGED BY ε TEST (ε = 0.001)
−∞ ≤ χ ≤ +∞

$\chi^2$ = 4.848e−07
base = 0
f = 0.03778 ± 0.0008
tau_f = 55.7 ± 5.3
amp_s = 0.8097 ± 0.0083
tau_s = 5.59e+03 ± 1.8e+02

$\chi^2$/2 = 0.0116
Intens = 154
ResAveMax = 0.00268
DurWatStat = 2.02
Lens =
Loc =

DELAYED BASELINE FOR FIT

METHOD AND APPARATUS FOR DETECTING CATARACTOGENESIS

TECHNICAL FIELD

The present invention relates to a method and apparatus for detecting diseases, and more particularly, to a method and apparatus for detecting diseases by inspecting ocular tissue.

BACKGROUND OF THE INVENTION

A reliable, quantitative and non-invasive method for the characterization of the molecular changes associated with early cataractogenesis in-vivo has long been an important goal of human clinical cataract research. Such a method would allow researchers and physicians to: (a) assess the effectiveness of putative anticataract reagents; (b) evaluate the cataractogenic role of pharmacologic agents or radiation used in the treatment of systematic diseases; (c) characterize early cataract in epidemiologic studies of human or animal populations subject to differential cataractogenic stress; and (d) provide a quantitative basis for the medical decision to intervene surgically or pharmaceutically in the treatment of cataract.

In 1975, T. Tanaka and G. Benedek ("Observation of Protein Diffusivity in Intact Human and Bovine ]Lenses with Application to Cataract," *Invest. Opthal*, 14, 1985, pp. 449–456) showed that the Brownian motion of proteins in excised human and bovine lenses could be measured optically using the method of quasielastic light scattering spectroscopy. Following this work, T. Tanaka and C. Ishimo to ("In Vivo Observation of Lens Protein Diffusivity in Normal and X-Irradiated Rabbit Lenses," *Exp. Eye Res.*, 39, 1984, pp. 61–68) demonstrated that quasielastic light scattering could be used in vivo in the rabbit to detect changes in mean protein diffusivity as a function of position and age in the lens. Further observations showed that the cataractogenic insult of x-irradiation upon the rabbit lens produced dramatic changes in the form of the autocorrelation function of the scattered light at a very early stage in the cataractogenic process. This change in the autocorrelation function, the mathematical heart of quasielastic light scattering analysis, demonstrated that the x-irradiation was responsible for drastic changes in the diffusivity of the protein scattering elements undergoing Brownian movement within the ocular tissue. Both Nishio and the 1977 Tanaka team observed that these altered correlation functions had a form different from that expected for the Brownian motions of a single-type scatterer. However, neither understood a quantitative analysis of the formation contained in the non-exponential character of the autocorrelation function observed.

In 1986, T. Libondi et al. ("In Vivo Measurement of the Aging Rabbit Lens Using Quasielastic Light Gathering," *Curr. Eye. Res.*, Vol. 5, No. 6, 1986, pp. 411–419) showed that the form of the autocorrelation function of the scattered light from a living rabbit eye indicated the presence of at least two distinct diffusing aspects within the rabbit lens. One species had a diffusivity corresponding to the a-crystalline protein. The other was a much more slowly diffusing species of the type discovered in vitro by M. Delaye et al. ("Identification of the Scattering Elements Responsible for Lens Opacification in Cold Cataracts," *Biophys. J.*, 37, 1982, pp. 647–656) in 1982.

A recently discovered method of cataract detection comprises irradiating a measurement location of a lens with a laser and collecting light scattered from the lens at the measurement location. The collected light is then analyzed using an autocorrelator or spectrum analyzer to determine the relative amount of light scattered from different protein species in the lens, and the relative light data are analyzed to determine the degree of cataract formation at the measurement location in the lens. A more detailed description of the method is given in U.S. Pat. No. 4,957,113, issued Sep. 18, 1990.

SUMMARY OF THE INVENTION

It is an object of the present invention to provide a method and an apparatus that account for the presence of slowly moving scatterers at the measurement location of ocular tissue.

It is another object of the present invention to provide a method and an apparatus that account for the presence of very slowly moving scatterers at the measurement location of ocular tissue.

It is a further object of the present invention to provide a method and an apparatus that can detect cataractogenesis in an individual subject in an in vivo manner through the computation of an autocorrelation of the fluctuations in the light scattered from slowly or very slowly moving particles in the ocular tissue of the individual.

It is a still further object of the present invention to provide a method and an apparatus that can detect cataractogenesis in an individual subject in an in vivo manner through the comparison of the value of one or more parameters measured in the individual to a frequency distribution of the same parameters in a population of subjects.

It is yet another object of the present invention to provide a method and an apparatus that can detect cataractogenesis in an individual subject in an in vivo manner through the detected change of the value of one or more parameters measured in the individual.

In one aspect, the present invention pertains to a method for in vivo detection of cataractogenesis in ocular tissue. The method comprises the steps of (a) producing a substantially monochromatic, coherent, collimated light, (b) causing the light to impinge on the ocular tissue; and (c) collecting light that is scattered from the ocular tissue. The method further comprises the steps of (d) performing a correlation analysis on the collected light to determine a signature of cataractogenesis, the signature including a dimensionless parameter $F_{mos}$ and a diffusion decay time parameter $(\tau_S)$, where $F_{mos}$ is a measure of the proportion of the intensity of the light scattered by particles in the ocular tissue that move slowly relative to the diffusion speed of other particles in the ocular tissue and $\tau_S$ is the diffusion decay time of the particles that move slowly relative to the diffusion speed of the other particles in the ocular tissue, and (e) detecting cataractogenesis from the signature.

In another aspect, the invention is an apparatus for in vivo detection of cataractogenesis in ocular tissue. The apparatus comprises a light source producing substantially monochromatic, coherent, collimated light, optics directing the light to impinge on the ocular tissue, and a light collector collecting light that is scattered from the ocular tissue. The apparatus further comprises electrical circuitry performing a correlation analysis on the collected light to determine a signature of cataractogenesis, the signature including a dimensionless parameter $F_{mos}$ and a diffusion decay time parameter ($\tau_S$), where $F_{mos}$ is a measure of the proportion of the intensity of the light scattered by particles in the ocular tissue that move slowly relative to the diffusion speed of other particles in the ocular tissue and $\tau_S$ is the diffusion decay time of the particles that move slowly relative to the diffusion speed of the other particles in the ocular tissue, and electrical circuitry detecting cataractogenesis from the signature.

In a further aspect, the invention is a method for in vivo detection of cataractogenesis in ocular tissue of an individual subject. The method comprises the steps of:

1. For each subject in a population of subjects, producing substantially monochromatic, coherent, collimated light, causing the light to impinge on the subject's ocular tissue, collecting light that is scattered from the ocular tissue, and performing a correlation analysis on the collected light to determine a signature of cataractogenesis, the signature including a dimensionless parameter $F_{mos}$ and a diffusion decay time parameter ($\tau_S$), where $F_{mos}$ is a measure of the proportion of the intensity of the light scattered by particles in the ocular tissue that move slowly relative to the diffusion speed of other particles in the ocular tissue and $\tau_S$ is the diffusion decay time of the particles that move slowly relative to the diffusion speed of the other particles in the ocular tissue;

2. developing a frequency distribution of at least one of the parameters;

3. for the individual subject, producing substantially monochromatic, coherent, collimated light, causing the light to impinge on the individual subject's ocular tissue; collecting light that is scattered from the individual subject's ocular tissue, and performing a correlation analysis on the collected light to determine a signature of cataractogenesis, the signature including a dimensionless parameter $F_{mos}$ and a diffusion decay time parameter ($\tau_S$), where $F_{mos}$ is a measure of the proportion of the intensity of the light scattered by particles in the ocular tissue that move slowly relative to the diffusion speed of other particles in the ocular tissue and $\tau_S$ is the diffusion decay time of the particles that move slowly relative to the diffusion speed of the other particles in the ocular tissue; and 4. determining a rate of cataractogenesis for the individual subject, based on the position of the value of at least one variable for the individual subject relative to the frequency distribution for that variable.

In a still further aspect, the invention comprises an apparatus for in vivo detection of cataractogenesis in ocular tissue of an individual subject. The apparatus comprises:

means for analyzing the ocular tissue of the individual subject, at a first time, the means including a light source for producing substantially monochromatic, coherent, collimated light, optics for directing the light to impinge on the ocular tissue of the individual subject, a light collector for collecting light that is scattered from the ocular tissue of the individual subject, and electrical circuitry for performing a correlation analysis on the collected light to determine a signature of cataractogenesis, the signature including a dimensionless parameter $F_{mos}$ and a diffusion decay time parameter ($\tau_S$), where $F_{mos}$ is a measure of the proportion of the intensity of the light scattered by particles in the ocular tissue that move slowly relative to the diffusion speed of the other particles in the ocular tissue;

means for analyzing the ocular tissue of the individual subject at a second time following the first time, the means including a light source for producing substantially monochromatic, coherent, collimated light, optics for directing the light to impinge on the ocular tissue of the individual subject, a light collector for collecting light that is scattered from the ocular tissue of the individual subject, and electrical circuitry for performing a correlation analysis on the collected light to determine a signature of cataractogenesis, the signature including a dimensionless parameter $F_{mos}$ and a diffusion decay time parameter ($\tau_S$), where $F_{mos}$ is a measure of the proportion of the intensity of the light scattered by particles in the ocular tissue that move slowly relative to the diffusion speed of other particles in the ocular tissue and $\tau_S$ is the diffusion decay time of the particles that move slowly relative to the diffusion speed of the other particles in the ocular tissue;

apparatus for determining the rate of change of at least one of the variables of the individual subject's ocular tissue as a function of age;

means for analyzing the ocular tissue of each individual in a population of individuals at a third time, the means including a light source for producing substantially monochromatic, coherent, collimated light, optics for directing the light to impinge on the ocular tissue of each individual subject, a light collector for collecting light that is scattered from the ocular tissue of each individual subject, and electrical circuitry for performing a correlation analysis on the collected light to determine a signature of cataractogenesis, the signature including a dimensionless parameter $F_{mos}$ and a diffusion decay time parameter ($\tau_S$), where $F_{mos}$ is a measure of the proportion of the intensity of the light scattered by particles in the ocular tissue that move slowly relative to the diffusion speed of other particles in the ocular tissue and $\tau_S$ is the diffusion decay time of the particles that move slowly relative to the diffusion speed of the other particles in the ocular tissue; and electrical circuitry comparing the rate of change of the at least one variable for the particular individual subject to the normal value of the rate of change with age of the at least one variable for the population of subjects to detect cataractogenesis in the ocular tissue of the individual subject.

In an even further aspect, the invention comprises a method for quantifying the location of a feature of a light beam passing through a material along a path having an entry point into the material and an exit point out of the material. The method comprises the steps of (a) viewing the material through a reticle from a position away from the path, the reticle having a series of circles formed thereon, the circles being concentric about a predetermined point on the reticle and having known radii, (b) adjusting the position of the reticle so that the feature of the light beam is coincident with the predetermined point and the entry and exit points are located within the series of circles, (c) reading the radii of the circles to determine a radius of the entrance point ($R_{ent}$) from the predetermined point, (d) reading the radii of the circles to determine a radius of the exit point ($R_{exit}$) from the predetermined point, and (e) computing the quantity f which is a function of at least one of $R_{ent}$ and $R_{exit}$.

In an even still further aspect, the invention comprises an apparatus for quantifying the location of a feature of a light beam passing through a material along a path having an entry point into the material and an exit point out of the material. The apparatus comprises an optical system to view the material through a reticle from a position away from the path, the reticle having a series of circles formed thereon, the circles being concentric about a predetermined point on the reticle and having known radii, means for adjusting the position of the reticle so that the feature of the light beam is coincident with the predetermined point and the entry and exit points are located within the series of circles, means for reading the radii of the circles to determine a radius of the entrance point ($R_{ent}$) from the predetermined point, means for reading the radii of the circles to determine a radius of the exit point ($R_{exit}$) from the predetermined point, and means for computing the quantity f which is a function of at least one of $R_{ent}$ and $R_{exit}$.

The above and other features of the invention, including various novel details of combination of parts, will now be more particularly described and pointed out in the claims. It will be understood that the particular cataractogenesis detection method and apparatus embodying the invention are shown by way of illustration only, and not as limitations of the invention. The principles and features of this invention may be employed in various and numerous embodiments without departing from the scope of the invention.

BRIEF DESCRIPTION OF THE DRAWINGS

FIG. 5A is the graph of a sample double exponential autocorrelation function and its best fit.

FIG. 5B is a graph of the residual errors between the sample double exponential autocorrelation function and the best fit shown in FIG. 5A.

FIG. 5C is a table of various estimates of the two parameter autocorrelation function and various conventional statistical measures of the goodness of fit between the sample double exponential autocorrelation function and the best fit shown in FIG. 5A.

DETAILED DESCRIPTION OF THE INVENTION

Figure 1:
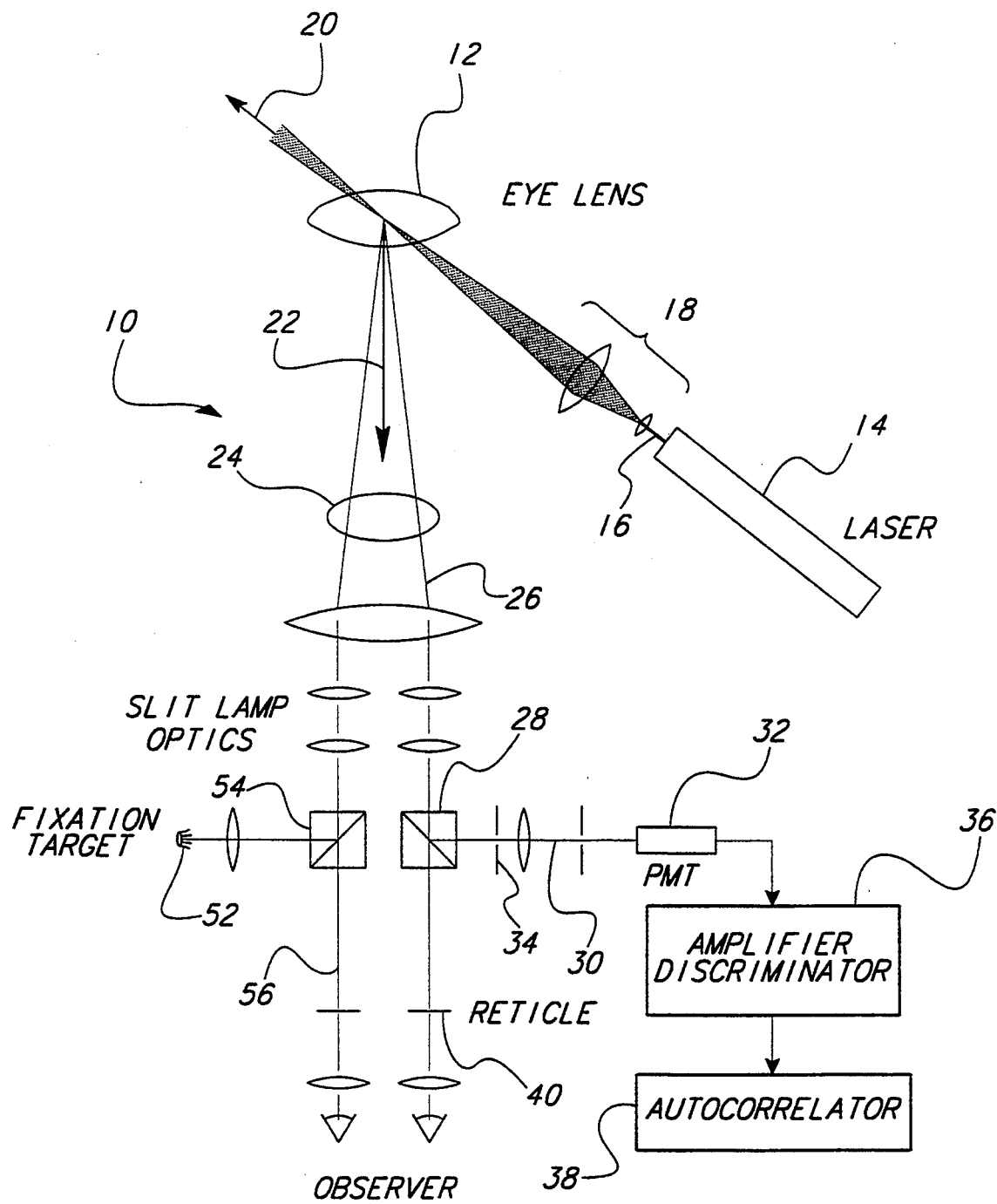
FIG. 1 is a schematic representation of an optical scattering analyzer for the study of light scattered in vivo from the lens of a subject.

The proteins present in ocular tissue undergo random diffusive movement due to continuous collisions with nearby molecules. When a coherent, steady beam of light is scattered by the moving proteins, the intensity of the scattered light fluctuates in time. The movements of the proteins determine the rate of intensity fluctuation. It has been determined that small proteins generally diffuse faster than larger proteins or protein aggregates, while immobile proteins do not diffuse at all. Small and large proteins have recently been determined to have respective diffusivites of $D_S = 1.5$ to $4 \times 10^{-9}$ cm²/sec and $D_f = 2.5$ to $3.5 \times 10^{-7}$ cm²/sec. Slow moving proteins move at speeds of approximately one wavelength of light per millisecond. Thus, it is possible to examine the current fluctuations in the output of a photomultiplier detector to determine the relative intensity of light scattered from the small protein species, the large protein species and the immobile protein species within the lens tissue. It is also possible to determine the relative amounts of these three species and the diffusivities of the two mobile species.

The various aspects of the present invention were developed in a clinical study involving 208 subjects, ages 17 to 63. The age dependence of autocorrelation functions of the photomultiplier detector currents was studied, and clear in vivo evidence for increased association of protein with age was found. The participants in the study were patients awaiting irradiation for bone marrow transplant (BMT), BMT donors, and volunteers, as part of a larger quasielastic light scattering (QLS) study on the lens effects of total body irradiation. The study population composition is shown below in Table 1.

| Age range in years | BMT patients | BMT donors | Volunteers | Totals |
| --- | --- | --- | --- | --- |
| <20 | 2 | 1 | 0 | 3 |
| 20 to 30 | 16 | 18 | 17 | 51 |
| 30 to 40 | 33 | 23 | 11 | 67 |
| 40 to 50 | 26 | 14 | 9 | 49 |
| 50 to 60 | 20 | 10 | 3 | 33 |
| >60 | 0 | 4 | 1 | 5 |
| Totals | 97 | 70 | 41 | 208 |

The aggregation of small proteins within the lens is the very first stage in the process of cataractogenesis. By using information obtained from the light scattered by the various fast and slow moving and immobile protein species, it is possible to interpret, in a clear and unambiguous manner, the meaning of the components contained in the autocorrelation function. More recently, it has been learned that analyses of slow-moving or very slow-moving particles within the lens are sufficient to detect the presence and/or rate of increase of cataractogenesis in the lens. This invention permits the decoding of the information contained in the random intensity fluctuations in the light scattered from the lens. The decoded information has been shown clinically to provide an accurate quantitative measure of cataract development on a molecular level long before it could be detected visually by either the subject or the physician.

Brownian motion is defined as the motion of macromolecules caused by thermal agitation and the random striking by neighboring molecules in a solution. In the lens of the human eye, protein molecules undergoing Brownian motion may be recorded and analyzed by quasielastic light scattering.

In quasielastic light scattering (QLS), the temporal fluctuations in intensity of light scattered by a selected small volume in the lens which is illuminated by an incident laser beam are studied. The scattered light intensity fluctuates in time because of the Brownjan motion of the scattering elements. In the case in which the laser beam illuminates the lens of the eye, the scattering elements are the molecular constituents of the fiber cells within the lens. These constituents are principally globular proteins called crystallins.

The light intensity fluctuations are detected by collecting the light scattered from a well defined, illuminated volume in the eye lens and focusing this light onto the surface an optical square law detector such as a photomultiplier tube or solid-state photodiode. The output of the detector is a photoelectric current whose temporal fluctuations are synchronized with the fluctuations in the scattered light intensity. The temporal fluctuations in the photocurrent can be analyzed mathematically by obtaining the autocorrelation function of the photocurrent. From the mathematical form of the autocorrelation function of the photocurrent, it is possible to determine the diffusivity of the scattering elements undergoing Brownjan movement.

The autocorrelation function may be determined by using an autocorrelator to analyze the fluctuations in the intensity of the laser light scattered by the ocular tissue. The random motions of the crystalline proteins within the lens give rise to concentration fluctuations, which in turn give rise to fluctuations in the intensity of the scattered light. This scattered light may be recorded in the form of a time correlation function, the autocorrelation function $C(\tau)$, which relates the scattered light intensity at a time t, I(t), to that a certain time $\tau$ later, $I(t+\tau)$, as follows: $C(\tau) = <I(t)I(t+\tau)>$, where $<>$ denotes averaging over all starting times t.

In practice, the foregoing calculation of the autocorrelation function can be accomplished as follows:

Let t denote elapsed time during a given measurement of duration T. Let $n(t_i)$ denote the number of detected photomultiplier pulses occurring in the time interval $i\Delta t < t < (i+1)\Delta t$, for sample time $\Delta t$. Let $I = T/\Delta t$ and $j = \tau_j/\Delta t$, where $\tau_j$ denotes the delay time interval. The autocorrelation functions $C(\tau)$ obtained represent the quantity $$C(\tau) = \sum_{i=1}^{I-j} n(t_i)n(t_i + j\Delta t) \quad (1)$$

The autocorrelation functions calculated are preferably transformed in one of three (or more) possible normalization-like manners involving a baseline. The autocorrelation function can be specifically normalized to $C_N(\tau) = (C(\tau) - B_{delay})/B_{delay}$, where $B_{delay}$ is the baseline and is calculated as the average of the autocorrelation function values obtained in eight delayed channels. Alternatively, the autocorrelation functions can be transformed by a calculated baseline $T\Delta t\, (I_{tot})^2$ or by a baseline that is fit to the empirical data by conventional numerical techniques.

One form of the temporal autocorrelation function has the following form:

$$C(\tau) = A[F_{mos}\exp(-\tau/\tau_S) + (1 - F_{mos})\exp(-\tau/\tau_f)]^2 + B, \quad (2)$$

where $\tau$ is a time delay variable, A is a constant representative of scattering in the absence of particles in the ocular tissue that move very slowly relative to the diffusion speed of the other particles in the ocular tissue, $F_{mos}$ is a measure of the proportion of the intensity of light scattered by particles in the ocular tissue that move slowly relative to the diffusion speed of other particles in the ocular tissue, and B is a baseline.

Alternatively, the temporal autocorrelation function can have the following form:

$$C(\tau) = \alpha_0[I_{mof}\exp(-\tau/\tau_f) + I_{mos}\exp(-\tau/\tau_S)]^2 + [I_{mof} + I_{mos} + I_{movs}]^2, \quad (3)$$

where $\tau$ is a time delay variable, and $\alpha_0$ is a predetermined constant representative of scattering in the absence of particles in the ocular tissue that move very slowly relative to the diffusion speed of other particles in the ocular tissue, $I_{mof}$ is the intensity of light scattered from the fast diffusing protein species or particles within the ocular tissue, $I_{mos}$ is the intensity of light scattered from the slow diffusing mobile protein species or particles within the ocular tissue, and $I_{movs}$ is the intensity of light scattered from very slow moving protein species or particles within the ocular tissue that diffuse very slowly with respect to the measurement time period of the autocorrelation measurement.

The value of A in equation 2 (or $\alpha_0$ in equation 3) may be determined from in vitro experiments in the absence of particles in the ocular tissue that move very slowly relative to the diffusion speed of other particles in the ocular tissue. Alternatively, the correlation measurements may be made on a solution of polystyrene spheres. The in vitro method for determining A or $\alpha_0$ may also be made on a solution of material isolated from an ocular lens containing substantially no particles that move very slowly relative to the diffusion speed of other particles in the tissue. Alternatively, the measurement of A in equation 2 (or $\alpha_0$ in equation 3) may be made by performing light scattering measurements on a population of individuals and choosing A (or $\alpha_0$) to be the maximum of the measured values for a particular parameter representative of the light scattering.

Each C(t) is fit to the form of $C_{Nfit}(\tau)$ by an algorithm which minimizes a measure of the deviation of the fitting function from the autocorrelator data obtained. One example of such an algorithm is the Marquardt nonlinear least squares algorithm (P. R. Bevington, *Data Reduction and Error Analysis for the Physical Sciences*, McGraw-Hill, New York, 1969, Chapter 11). The slow diffusion time $\tau_S = (1/D_S q^2)$, where $q = (4\pi n/\lambda)\sin(\theta/2)$, n = index of refraction of scattering volume and $D_s$ = diffusivity of slow scatterers. Similarly, $\tau_f = (1/D_f q^2)$ for fast scatterers, $F_{mos}$ = fraction of light scattered from mobile scatterers due to slow scatterers, and A is the amplitude of the time-dependent part of the autocorrelation function. $I_{tot}$, the average total intensity (the number of detected photons per unit time) was obtained for each measurement. Goodness of fit was judged by examination of the residuals versus delay time, $\tau$, for each of the 2000 autocorrelation functions recorded ninety-two and sixth tenths percent of the functions were judged to be good fits to the two-parameter autocorrelation form above. This qualitative evaluation agreed well with a quantitative evaluation of the significance of trends in the residuals made with use of the Durbin-Watson statistic (Neter, J., Wasserman, W. and Kutner, M. H. (1985), *Applied Linear Statistical Models*, Irwin, Homewood, Ill., Chapter 13).

In this study, the dependence on age of quasielastic light scattering parameters measured in vivo from portions of the human ocular lens (near the visual axis) was studied. The findings of the study are consistent with numerous earlier studies showing increased association of protein in the lens cytoplasm with increasing age. The probability distribution functions of the total scattered intensity $I_{tot}$ and the slow fraction $F_{mos}$, and the mean value of the slow diffusion time $\tau_S$, have been characterized as a function of age and location along the visual axis for this study population.

Certain aspects of this detailed description are discussed more fully in U.S. patent application No. 07/637,289, filed on Jan. 4, 1991, now issued U.S. Pat. No. 5,279,296. That patent is hereby incorporated by reference in the present application.

FIG. 1 is a schematic representation of an optical scattering analyzer 10 for the study of light scattered in vivo from the lens 12 of a subject. A helium-neon laser 14 of wave length 632.8 nm (source) is mounted on a modified slit lamp apparatus (not shown). The laser 14 produces a laser beam 16 which is attenuated through conventional optics 18 so as to provide for two incident intensities: one is an intensity of 170 microwatts used for measurement of the autocorrelation function, and the other is an intensity of 20 microwatts used for alignment purposes between measurements. The direction 20 of the laser beam 16 is fixed so as to result in an angle of 140 degrees between the direction 20 of propagation of the laser beam 16 onto the lens 12 and the direction 22 of propagation of the laser light 24 that is scattered by the lens 12. The laser beam 16 is focussed to a waist having an approximate diameter between $(1/e^2)$ points of 15 microns. Each measurement of the autocorrelation function is conducted within a 10 second period. The resulting irradiance is well within the guidelines of the American National Standards Institute for ocular exposure.

Within the measurement optical path 26 of the binocular slit lamp, a beam splitter 28 deflects a portion of the scattered light along the direction 22 so as to impinge on the end of a fiber optic 30, which relays the light to a photon-counting photomultiplier tube 32 (such as one manufactured by EMI). The photon-counting photomultiplier tube 32 produces a corresponding train of pulses. An aperture 34 was used to limit the detected scattering to originate from a portion of the beam which was 200 microns in length in the lens 12. An amplifier-discriminator 36 (such as one manufactured by Malvern Instruments) prepares the pulses produced by the photon-counting photomultiplier tube 32 for input to an autocorrelator 38 (also manufactured by Malvern Instruments). The autocorrelator 38, has 128 equally spaced channels and 8 delayed channels, and a sample time of 10 microseconds. The delayed channels were spaced by 10 microseconds starting at delay time 6400 microseconds. Autocorrelation functions calculated by the autocorrelator 38 are stored in the autocorrelator 38 for later analysis.

Figure 2:
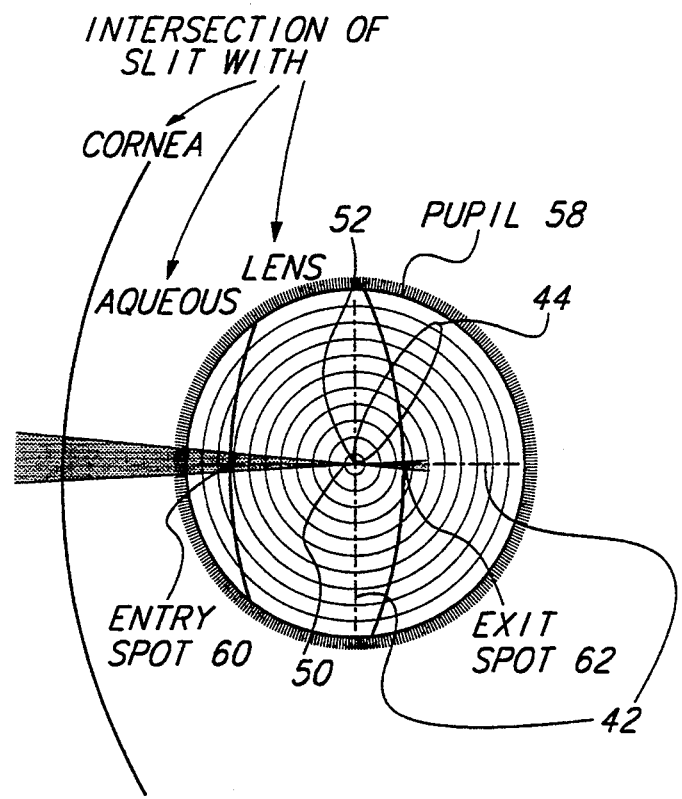
FIG. 2 is a schematic representation of the view as seen by an individual using the optical scattering analyzer shown in FIG. 2.
Figure 3:
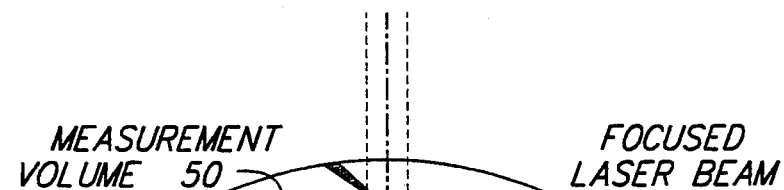
FIG. 3 is a cross-sectional view of a lens as seen from the direction of FIG. 1.

The scattered light that is undeflected by the beam splitter 28 is used to quantitate the position of the scattering volume within the lens 12, with use of a reticle 40 placed in the slit lamp ocular. The reticle 40 includes a cross-hair 42 centered within a set 44 of equally spaced, concentric circles. This is shown in FIG. 2 which is a schematic representation of the view as seen by an individual using the optical scattering analyzer 10 shown in FIG. 2. FIG. 3 is a cross-sectional view of a lens as seen from the direction of FIG. 1.

The optical scattering analyzer 10 is aligned so that the center of the measurement volume 50 in the lens 12 appears superimposed on the center 52 of the cross-hair 42. For in vivo measurements the patient can be asked to gaze at a green fixation source 52, which is projected with use of a beam splitter 54 into a slit lamp optical path 56 not being employed for detection of the light scattered by the lens 12. With use of the conventional slit lamp controls the instrument is then positioned so that the weak alignment laser beam described above enters and traverses the ocular lens 12, and so that both the pupil 58 of the eye and the measurement volume 50 to be measured appear concentric with the circles 44 of the reticle 40.

By dilating the pupils of the individual who is being measured it is usually possible to see the positions of entry spot 60 and the exit spot 62 of the laser beam 16 to and from the ocular lens 12, superimposed on the concentric circles 44 of the reticle 40. As shown in FIG. 2, from the observer's viewpoint the laser beam 16 enters the lens 12 from the right hand side. The apparent position (R) on the reticle 40 of the entry spot 60 is noted by the observer, in units of the number of circles to the right of the center of the reticle. The same was done for the apparent position (L) on the recticle 40 of the exit spot 62 of the beam 16, which appears to the left of the center 52 in the cross-hair 42 of the reticle 40. Both reticle readings are recorded and used on subsequent visits, if applicable, to return to the same measurement volume 50 within the ocular lens 12. With this protocol, measurements are made in positions close to the visual axis 62 of the eye, which is close to the observation direction, since the individual's gaze is fixed closely in direction to that of the measurement optical axis, and the pupil 58 was centered on the measurement volume 50. Measurements are carried out at fixed magnification of 25×.

Measurements are performed principally in three locations within the lens 12: anterior, nuclear and posterior. The positions of the measurements can be quantitated in terms of the following measure of their fractional distance along the measurement axis within the lens, $l = R/(R+L)$, so that $l=0$ corresponds to the anterior surface of the lens 12, and $l=1$ corresponds to the posterior surface of the lens 12. With use of these coordinates, the probability distribution function for the locations measured can be determined. Since the path of the laser beam 16 through the lens 12 is not necessarily a straight line, the form of the quantifying function l may be more complicated than that shown above. However, it will be a function of at least one of the variables designating the entrance and exit points of the laser beam 16.

Figure 4:
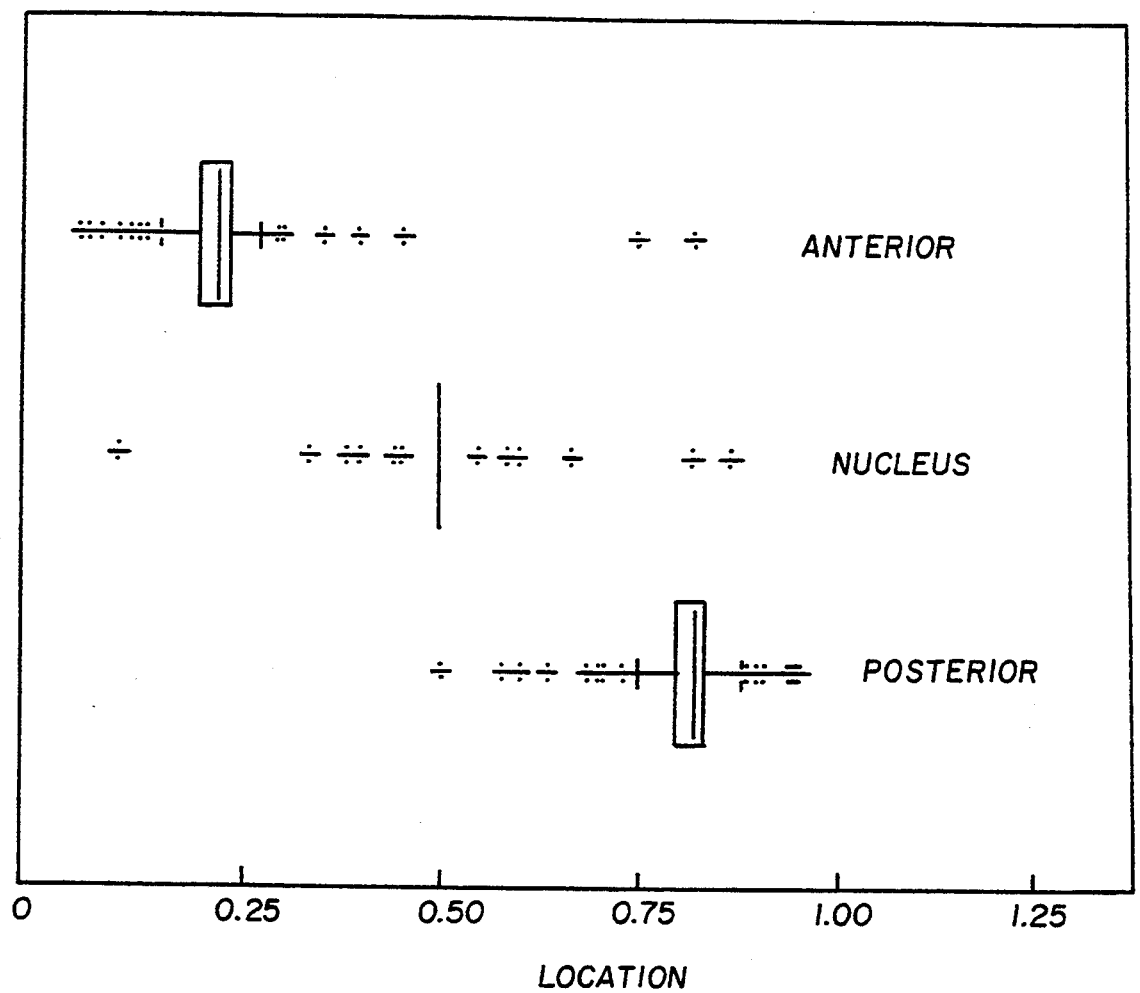
FIG. 4 is a graph of perceived locations of measurements versus quantitated locations of the measurements within a lens.

FIG. 4 is a graph of perceived locations of measurements versus quantitated locations of the measurements within a lens. At each recorded measurement location (anterior, nucleus, and posterior), the box spans the upper and lower quartiles, and its midline is the median. From FIG. 4 it can be seen that the anterior measurements corresponded principally to $0.1 < 1 < 0.3$, the nuclear measurement corresponded principally to $0.4 < 1 < 0.6$, and the posterior measurements corresponded principally to $0.75 < 1 < 0.9$.

FIG. 5A is the graph of a sample double exponential autocorrelation function and its best fit. The points 100 are the data samples. The curve 102 is the best-fitting double parameter autocorrelation function.

FIG. 5B is a graph of the residual errors between the sample double exponential autocorrelation function and the best fit shown in FIG. 5A. The points 110 are the values of the residuals between the respective points 100 and the curve 102 in FIG. 5A. It is clear that the curve 102 fits the data points 100 quite well.

FIG. 5C is a table of various estimates of the two parameter autocorrelation function and various conventional statistical measures of the goodness of fit between the sample double exponential autocorrelation function and the best fit shown in FIG. 5A.

During a given measurement and between measurements, relative motion of the measuring instrument and the eye occurs, and as a result, the measurement volume successively samples slightly different portions of the lens. This is one source of variation in the QLS parameters obtained upon successive measurements. Table 2 below gives the values of the square root of appropriate mean sums of squared errors (RMSSE), representing the reproducibility of measurements of $I_{tot}$, $F_{mos}$, $\tau_S$ and $\tau_f$ for successive measurements at the same reported location within a lens.

| Location | RMSSE for: | | | |
|---|---|---|---|---|
|  | $I_{tot}$ | $F_{mos}$ | $\tau_s$ | $\tau_f$ |
| anterior | 11 | 0.031 | 820 | 15 |
| nucleus | 16 | 0.039 | 940 | 16 |
| posterior | 61 | 0.034 | 1270 | 17 |

A higher fraction of functions taken from the posterior of the lens and from older subjects are non-double exponential, as shown in Table 3, below:

| Age range in years | anterior | nucleus | posterior |
|---|---|---|---|
| 20 to 30 | 0.04 | 0.03 | 0.04 |
| 30 to 40 | 0.02 | 0.02 | 0.15 |
| 40 to 50 | 0.03 | 0.02 | 0.21 |
| 50 to 60 | 0.02 | 0.07 | 0.39 |

Figure 6:
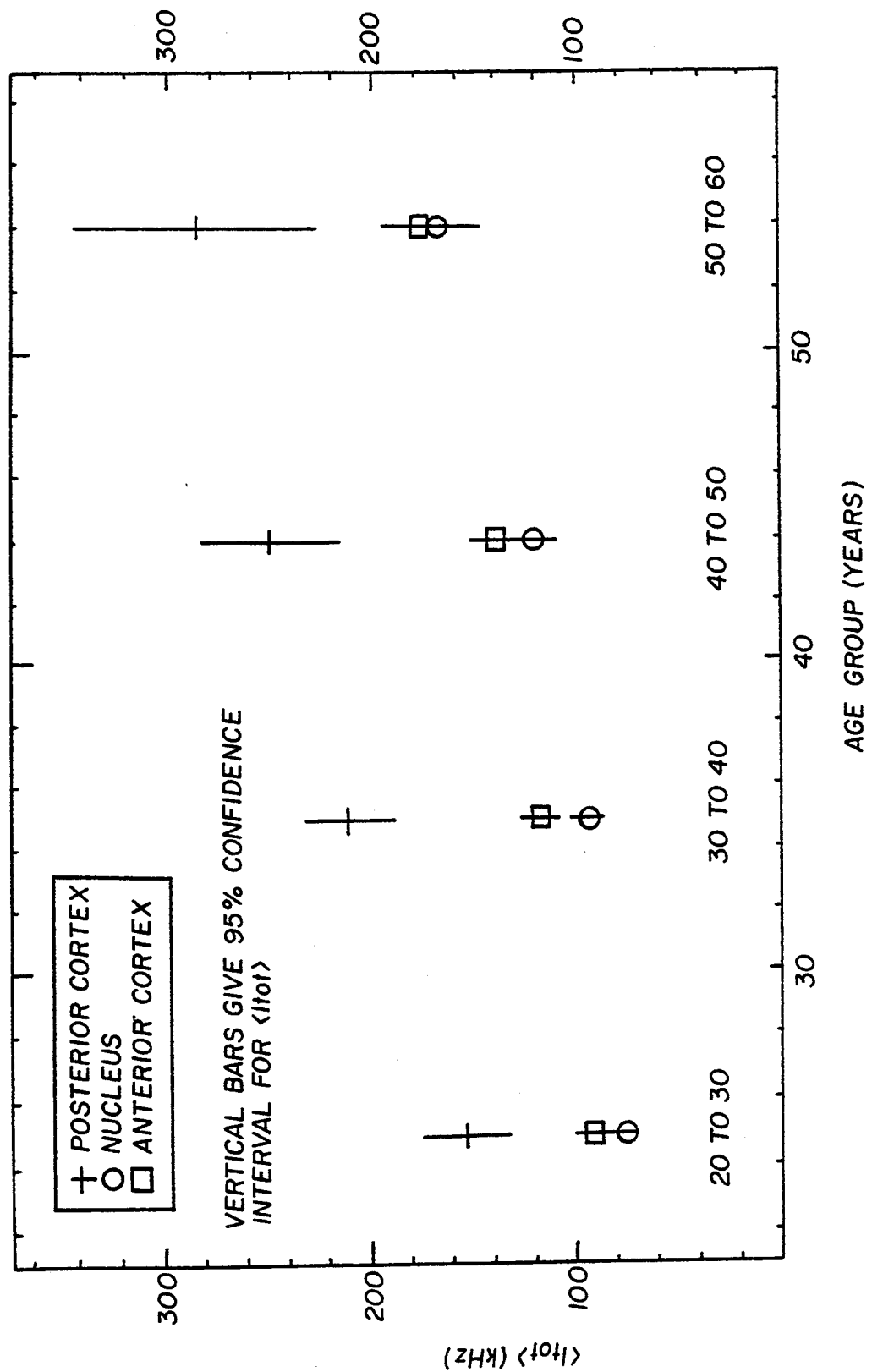
FIG. 6 is a graph of the mean total scattered intensity $<I_{tot}>$ as a function of subject age, for each of the three measurement locations.

FIG. 6 is a graph of the mean total scattered intensity $<I_{tot}>$ as a function of subject age, for each of the three measurement locations. The three measurement locations are the posterior cortex, the nucleus and the anterior cortex of the lens. The vertical bars give 95% confidence interval for $<I_{tot}>$ and each of the three measurement locations. At each of the three locations, it is clear that the mean total scatterer intensity $<I_{tot}>$ increases with age, and that $<I_{tot}>$ increases most rapidly with age at the posterior cortex.

It can be useful to compare the intensity of light scattered from the lens to the intensity of light scattered by other materials, since the materials can then be used for approximate cross-calibration of different light scattering instruments as well as for estimation of thermodynamic properties of the lens cytoplasm. The Rayleigh ratio $R() = I_{tot} r^2 / I_0 V$ gives the proportion of the incident light scattered in the direction, where $I_{tot}$ is the intensity scattered in the direction, $I_0$ is the intensity of the incident light source (assumed polarized in a direction perpendicular to the plane of the scattering), r is the distance from the scattering volume to the detecting medium, and V is the scattering (measurement) volume. Comparing the observed scattered intensities with those from toluene ($R_{toluene} = 4 \times 10^{-5}$ cm$^{-1}$), it is found that $I_{tot} = 100$ kHz on the present instrument corresponds to $R(140) = 2 \times 10^{-2}$ cm$^{-1}$. The Rayleigh ratio of a scattering medium can be found by first observing the intensity of scattering from a medium having a known Rayleigh ratio. One medium for this purpose is sufficiently purified toluene, which has a Rayleigh ratio of about $4 \times 10^{-5}$ cm$^{-1}$. The Rayleigh ratio of a medium can then be found simply by comparing the intensity scattered with the intensity scattered by toluene with appropriate corrections applied for the incident intensity and optical scattering geometry. These corrections will be known by those skilled in the art. For the present instrument, a comparison with toluene will correspond to $R(140) = 2 \times 10^{31\,2}$ cm$^{-1}$.

Figure 7:
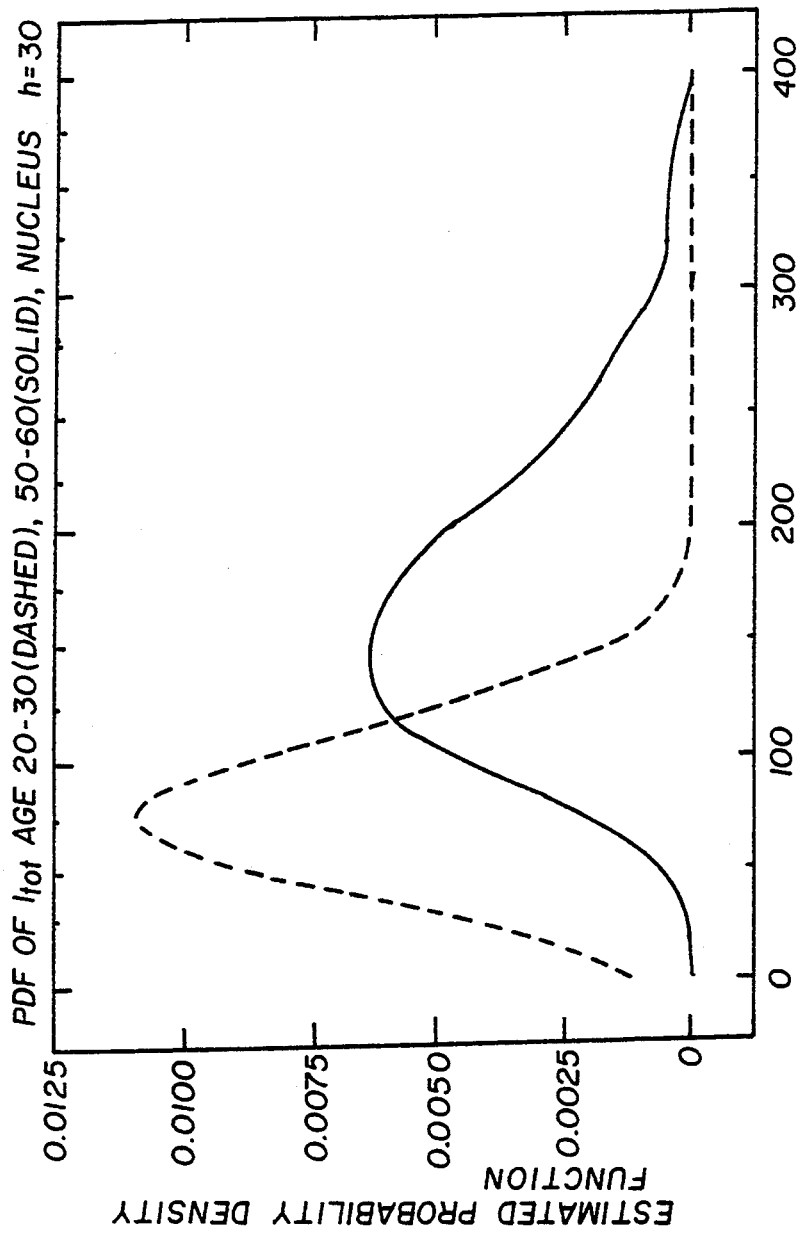
FIG. 7 is a graph of the probability distributions of $I_{tot}$, parameterized as a function of age.

FIG. 7 is a graph of the probability distributions of $I_{tot}$, parameterized as a function of age. For a given QLS parameter P, the probability density function f(P) may be estimated from the frequency data in a variety of ways, where f(x)dx is the probability that $x < P < x + dx$. The graph in FIG. 7 illustrates an estimate of $f(I_{tot})$ for the nucleus, for 20 to 30 year olds (dashed curve) and for 50 to 60 year olds (solid curve).

Figure 8:
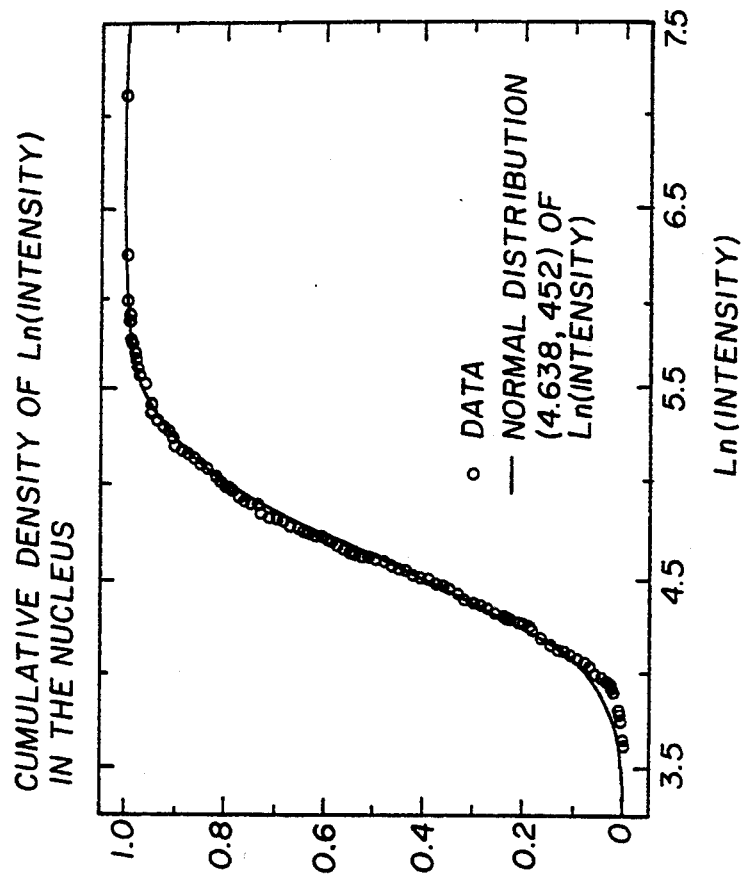
FIG. 8 is a graph of the cumulative density function of $\ln(I_{tot})$ for all measurements in the nucleus, compared to that of a normal distribution.

FIG. 8 is a graph of the cumulative density function of $\ln(I_{tot})$ for all measurements in the nucleus, compared to that of a normal distribution. It is interesting to note that the distribution of $I_{tot}$ can be approximated by a common, skew distribution, the log normal distribution. It is clear from FIG. 8 that this approximation is quite good.

Figure 9:
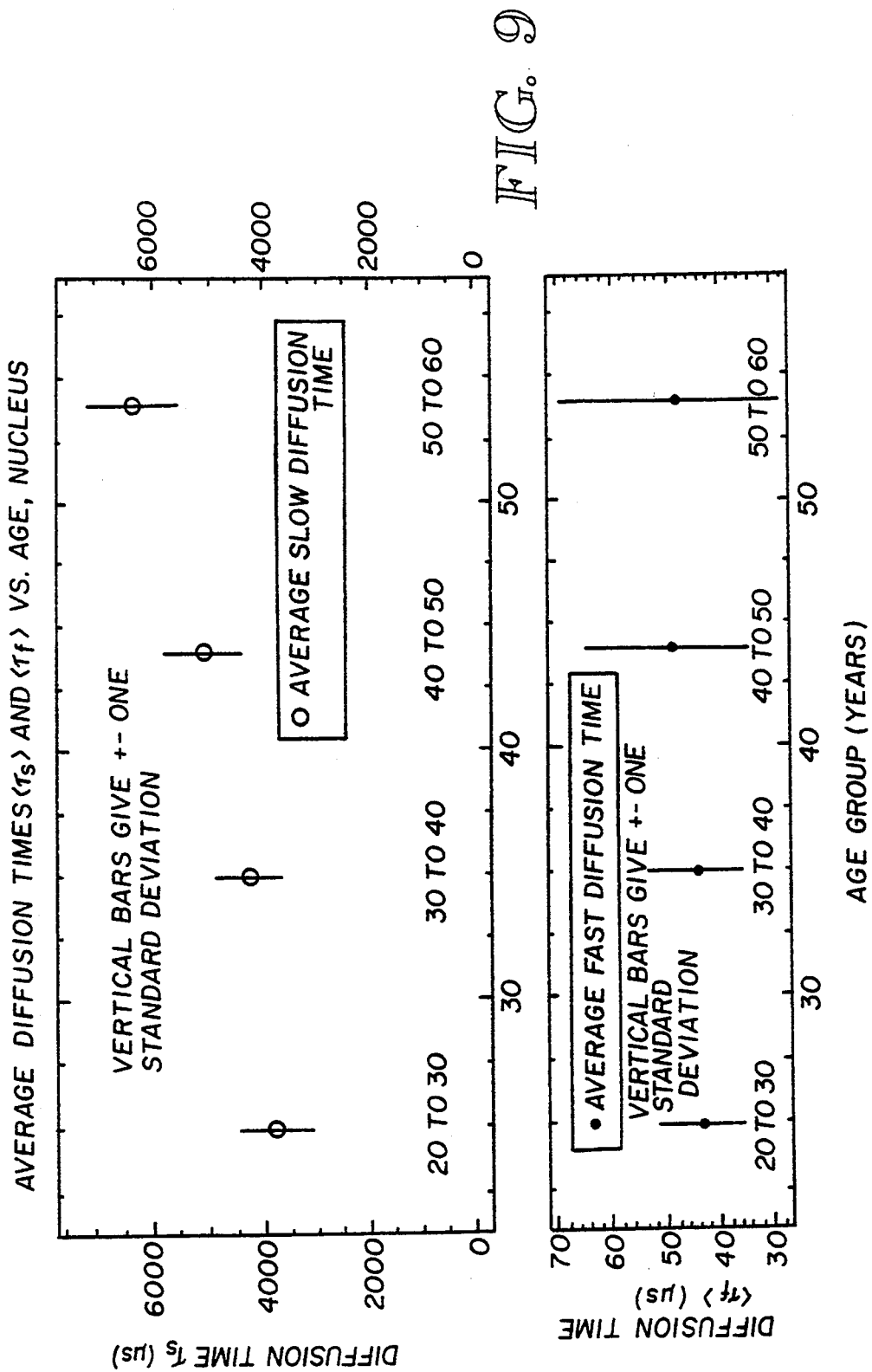
FIG. 9 is a graph of the average diffusion times $<\tau_S>$ and $<\tau_f>$ with age, in the nucleus.

FIG. 9 is a graph of the average diffusion times $<\tau_S>$ and $<\tau_f>$ with age, in the nucleus. From FIG. 9 it is clear that the slow diffusion time $\tau_S$ increases with age, while the fast diffusion time $\tau_f$ is relatively constant with age. The increase of the diffusion time $\tau_S$ is consistent with a decrease in the flow diffusivity $D_S$ and with increased protein association.

Figure 10:
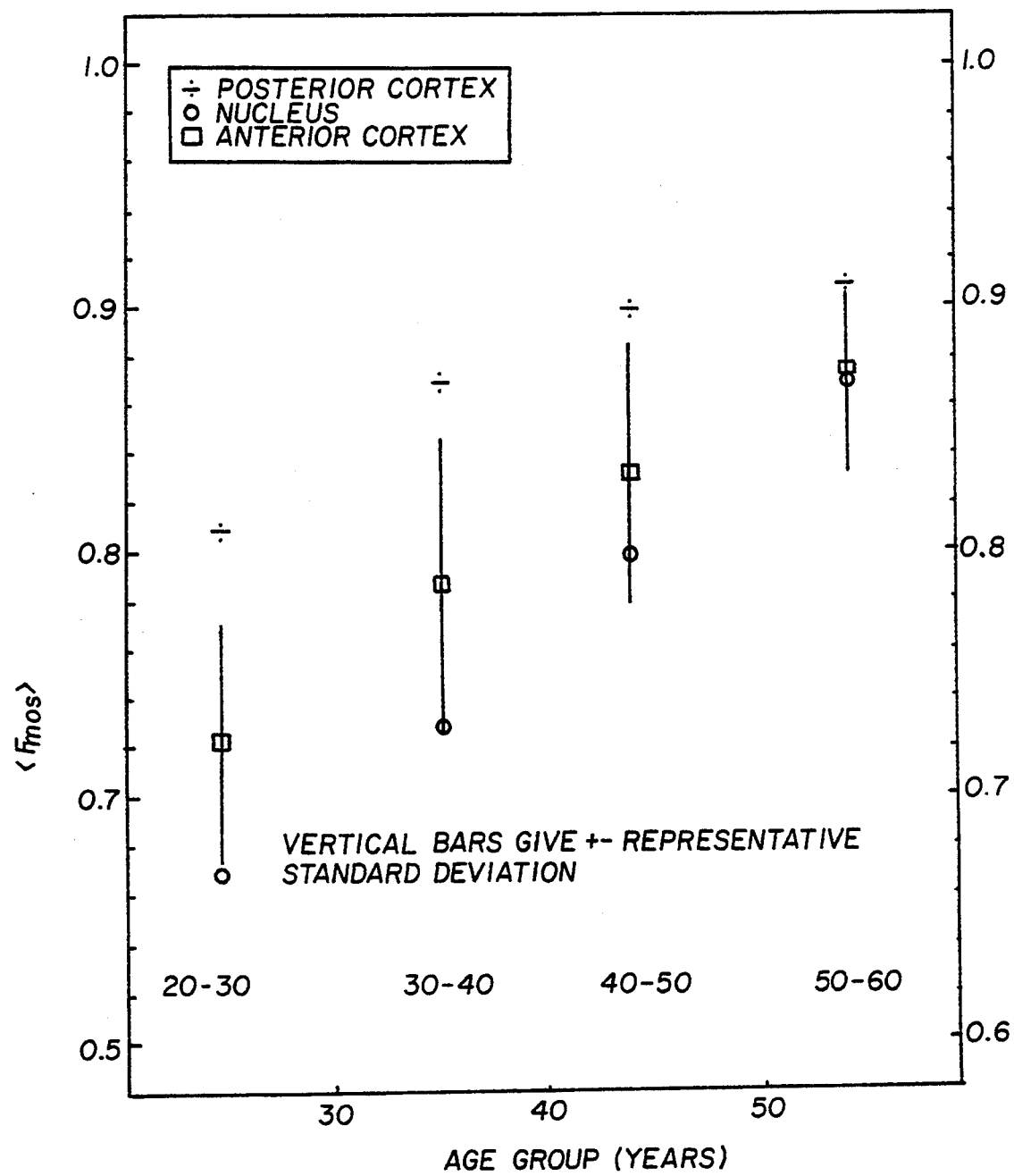
FIG. 10 is a graph of the average fraction of scattering from slowly diffusing mobile scatterers with age, for each of the three measurement locations.

FIG. 10 is a graph of the average fraction of scattering from slowly diffusing mobile scatterers with age, for each of the three measurement locations. It is clear that this parameter, $<F_{mos}>$, increases with age.

Figure 11:
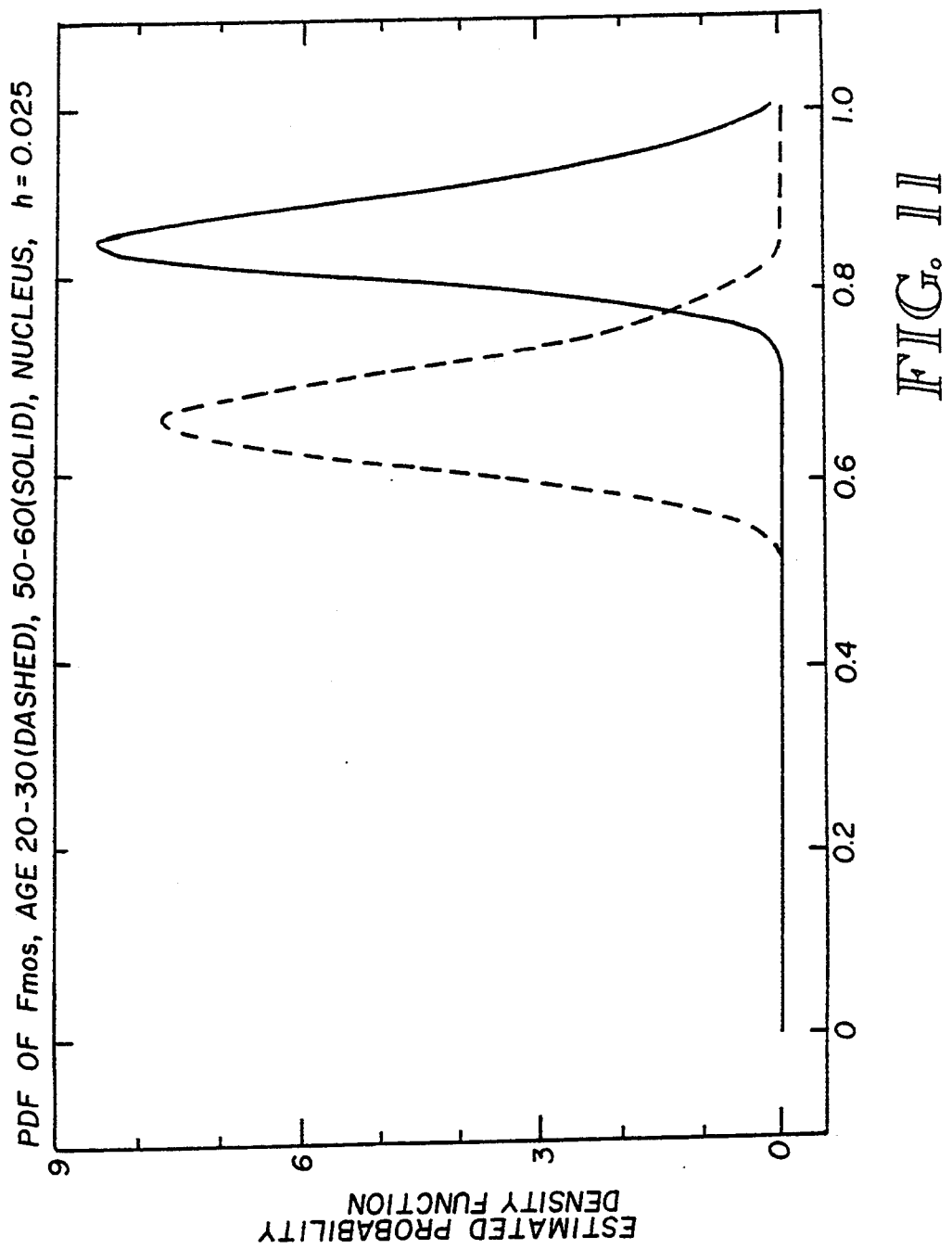
FIG. 11 is a graph of the probability density functions of $F_{mos}$, parameterized as a function of age.
Figure 12:
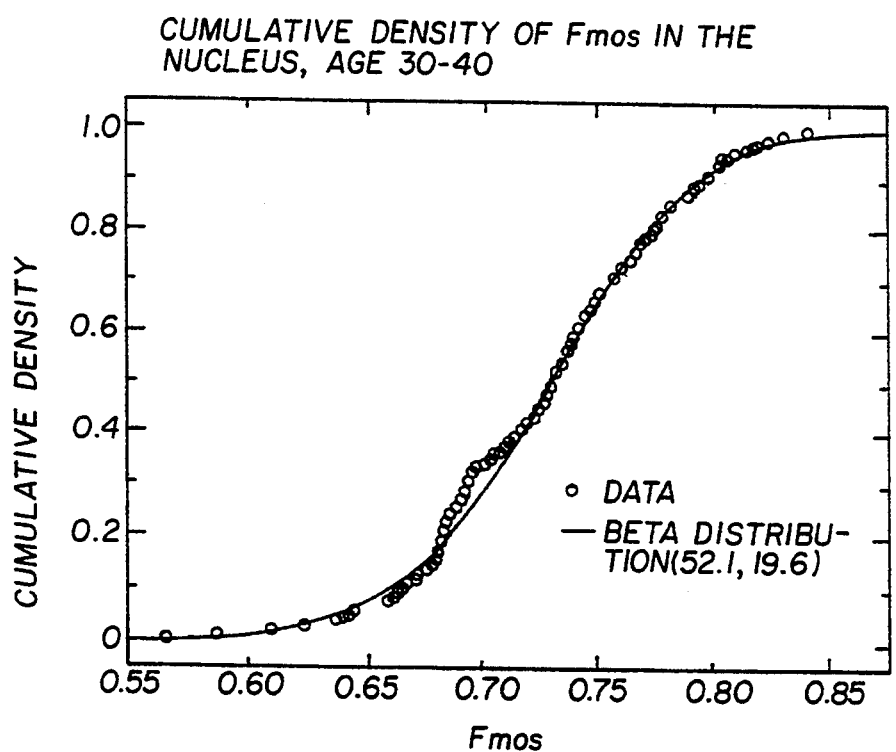
FIG. 12 is a graph of the distribution of $F_{mos}$ for 30 to 40 year olds in the nucleus, compared to that of a beta distribution.

FIG. 11 is a graph of the probability density functions of $F_{mos}$, parameterized as a function of age. The two probability distributions $f(F_{mos})$ are shown for the nucleus, for 20 to 30 year olds (dashed curve) and for 50 to 60 year olds (solid curve). The probability distribution of $F_{mos}$ shifts clearly towards more slow mobile scattering with increasing age. FIG. 12 is a graph of the distribution of $F_{mos}$ for 30 to 40 year olds in the nucleus, compared to that of a beta distribution. It is clear that the beta distribution is a good approximation to the distribution of $F_{mos}$.

Figure 13:
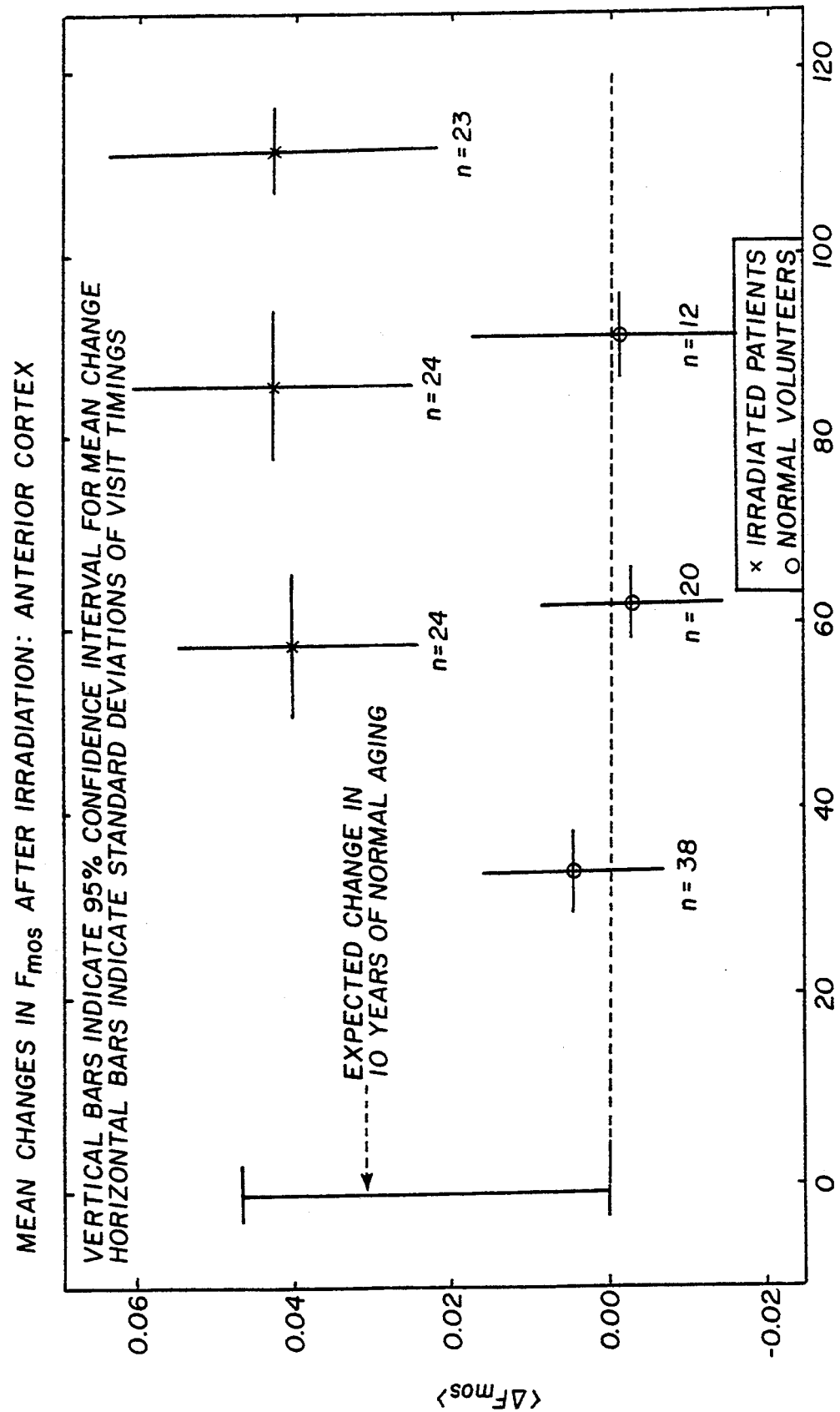
FIG. 13 is a graph of the average change in $F_{mos}$ in the anterior cortex within 60 days after irradiation, for unirradiated volunteers and for ten years of normal aging.

FIG. 13 is a graph of the average change in $F_{mos}$ in the anterior cortex within 60 days after irradiation, for unirradiated volunteers and for ten years of normal aging. Patients were measured before receiving about 1500 rads total body irradiation, fractionated over 5 or 6 days. In this group, 20 to 60% have been found to develop cataracts within a ten year period. The graph shows that the average change in $F_{mos}$ in the anterior cortex was significant within 60 days after irradiation for the 24 bone marrow transplant patients, who had three visits after irradiation. The mean change in $F_{mos}$ after irradiation is positive and small, but statistically significant. This shows that QLS is capable of discerning significant changes in protein association in the ocular lens, shortly after the cataractogenic insult of total body irradiation.

It should be noted that a frequency distribution of the parameters $\tau_s$ and $F_{mos}$ can be produced by performing the measurements previously described for each subject in a population of subjects, and that a rate of change of cataractogenesis in an individual subject can be determined by performing the measurements previously described and determining the rate of cataractogenesis for the individual based on the position of the value of at least one of the above variables for the individual subject relative to the frequency distribution for that variable. The frequency distribution may be determined using the parameter $F_{mos}$, the parameter $\tau_s$, or both.

A rate of change of cataractogenesis can be determined by performing the above-described measurements on an individual on two separate occasions and performing a correlation analysis on the collected light to determine a signature of cataractogenesis that includes the dimensionless parameter $F_{mos}$ and the diffusion decay time parameter $\tau_s$ where $F_{mos}$ is a measure of the proportion of the intensity of the light scattered by particles in the ocular tissue that move slowly relative to the diffusion speed of other particles in the ocular tissue, and $\tau_s$ is the diffusion decay time of the particles that move slowly relative to the diffusion speed of other particles in the ocular tissue. The rate of change with individual age of at least one of those variables for a particular individual is compared to the normal value of the rate of change with age of that variable for the population of subjects to detect cataractogenesis in the ocular tissue of the individual subject. The rate of change of the variable $F_{mos}$ can be used to determine the degree of cataractogenesis.

Those skilled in the art will recognize, or be able to ascertain, using no more than routine experimentation, many equivalents to the specific embodiment of the invention described herein. For example, the delivery, observation, control and collection optics are not intended to be solely limited to the embodiments described herein, but rather are intended to extend to any optical system suitable for these purposes. Such equivalents are intended to be encompassed by the following claims.

We claim:

1. A method for in vivo detection of cataractogenesis in ocular tissue, comprising the steps of:
    (a) producing a substantially monochromatic, coherent, collimated light;
    (b) causing the light to impinge on the ocular tissue;
    (c) collecting light that is scattered from the ocular tissue;
    (d) performing a correlation analysis on the collected light to determine a signature of cataractogenesis, the signature including a dimensionless parameter $F_{mos}$ and a diffusion decay time parameter ($\tau_S$), where $F_{mos}$ is a measure of the proportion of an intensity of the light scattered by particles in the ocular tissue that move slowly relative to a diffusion speed of other particles in the ocular tissue and $\tau_S$ is a diffusion decay time of the particles that move slowly relative to the diffusion speed of the other particles in the ocular tissue; and
    (e) detecting cataractogenesis from the signature.

2. The method of claim 1 wherein step (c) comprises collecting the light that is scattered from the ocular tissue over a time period and step (d) comprises computing a temporal autocorrelation function of the collected light.

3. The method of claim 2 wherein step (d) further comprises performing a least squares analysis on the temporal autocorrelation function to determine the functional form of the function $C(\tau)$ which best fits the temporal autocorrelation function, where $$C(\tau) = A\ ]F_{mos}exp(-\tau/\tau_S) + (1-F_{mos})exp(-\tau/\tau_f)^2 + B,$$

$\tau$ is a time delay variable, A is a constant representative of scattering in the absence of particles in the ocular tissue that move very slowly relative to the diffusion speed of the other particles in the ocular tissue and B is a baseline.

4. The method of claim 3, further comprising the step of:
    (f) determining the value of A from in vitro experimentation in the absence of particles in the ocular tissue that move very slowly relative to the diffusion speed of the other particles in the ocular tissue.

5. The method of claim 4 wherein step (f) comprises making correlation measurements on a solution of polystyrene spheres.

6. The method of claim 4 wherein step (f) comprises making correlation measurements on a solution of material isolated from an ocular lens containing substantially no particles that move very slowly relative to the diffusion speed of the other particles in the tissue.

7. The method of claim 3, further comprising the step of:
    (f) making measurements of the value of a parameter representative of light scattering from the ocular lens of each member of a population of individuals and choosing a value of A to be the maximum of the measured values.

8. Apparatus for in vivo detection of cataractogenesis in ocular tissue, comprising:
    a light source producing substantially monochromatic, coherent, collimated light;
    optics directing the light to impinge on the ocular tissue;
    a light collector collecting light that is scattered from the ocular tissue;
    correlation means for performing a correlation analysis on the collected light to determine a signature of cataractogenesis, the signature including a dimensionless parameter $F_{mos}$ and a diffusion decay time parameter ($\tau_S$), where $F_{mos}$ is a measure of the proportion of an intensity of the light scattered by particles in the ocular tissue that move slowly relative to a diffusion speed of other particles in the ocular tissue and $\tau_S$ is a diffusion decay time of the particles that move slowly relative to the diffusion speed of the other particles in the ocular tissue; and
    analysis means for detecting cataractogenesis from the signature.

9. The apparatus of claim 8 wherein the light collector collects light that is scattered from the ocular tissue over a predetermined period of time, said correlation means comprising a computer programmed to compute a temporal autocorrelation function of the intensity of the collected light.

10. The apparatus of claim 9 wherein said correlation means comprises means for performing a least squares analysis on the temporal autocorrelation function to determine the functional form of the function $C(\tau)$ which best fits the temporal autocorrelation function, where $$C(\tau)=A$$
$$]F_{mos}exp(-\tau/\tau_S)+(1-F_{mos})exp(-\tau/\tau_f]^2+B,$$

$\tau$ is a time delay variable, A is a predetermined constant representative of scattering in the absence of particles in the ocular tissue that move very slowly relative to the diffusion speed of the other particles in the ocular tissue and B is a baseline.

11. The apparatus of claim 10, further comprising means for determining the value of A from in vitro experimentation in the absence of particles in the ocular tissue that move very slowly relative to the diffusion speed of the other particles in the ocular tissue.

12. The apparatus of claim 11 wherein said means for determining the value of A comprises means for making correlation measurements on a solution of polystyrene spheres.

13. The apparatus of claim 11 wherein said means determining the value of A comprises means for making correlation measurements on a solution of material isolated from an ocular lens containing substantially no particles that move very slowly relative to other particles in the tissue.

14. The apparatus of claim 10 further comprising parameter measurement means for making measurements of the value of a parameter representative of light scattering from the ocular lens of each member of a population of individuals and choosing a value of A to be the maximum of the measured values.

15. The apparatus of claim 8 wherein said correlation means comprises an integrated circuit for computing a temporal autocorrelation function of the intensity of the collected light.

16. The apparatus of claim 8 wherein said correlation means comprises a standalone autocorrelator for computing a temporal autocorrelation function of the intensity of the collected light.

17. A method for in vivo detection of cataractogenesis in ocular tissue of an individual subject, comprising the steps of:
  (1) For each subject in a population of subjects:
    (a) producing substantially monochromatic, coherent, collimated light;
    (b) causing the light to impinge on the subject's ocular tissue;
    (c) collecting light that is scattered from the ocular tissue; and
    (d) performing a correlation analysis on the collected light to determine a signature of cataractogenesis, the signature including a dimensionless parameter $F_{mos}$ and a diffusion decay time parameter ($\tau_S$), where $F_{mos}$ is a measure of the proportion of an intensity of the light scattered by particles in the ocular tissue that move slowly relative to a diffusion speed of other particles in the ocular tissue and $\tau_S$ is a diffusion decay time of the particles that move slowly relative to the diffusion speed of the other particles in the ocular tissue;
  (2) developing a frequency distribution of at least one of the parameters;
  (3) for the individual subject:
    (a) producing substantially monochromatic, coherent, collimated light;
    (b) causing the light to impinge on the individual subject's ocular tissue;
    (c) collecting light that is scattered from the individual subject's ocular tissue; and
    (d) performing a correlation analysis on the collected light to determine a signature of cataractogenesis, the signature including a dimensionless parameter $F_{mos}$ and a diffusion decay time parameter ($\tau_S$), where $F_{mos}$ is a measure of the proportion of an intensity of the light scattered by particles in the ocular tissue that move slowly relative to a diffusion speed of other particles in the ocular tissue and $\tau_S$ is a diffusion decay time of the particles that move slowly relative to the diffusion speed of the other particles in the ocular tissue; and
  (4) determining a rate of cataractogenesis for the individual subject, based on the position of a value of at least one variable for the individual subject relative to the frequency distribution for that variable.

18. The method of claim 17, wherein step (2) comprises developing a frequency distribution of exactly one of the parameters taken from the group of parameters comprising $F_{mos}$ and $\tau_S$.

19. The ;method of claim 18, wherein step (2) comprises developing a frequency distribution of exactly two of the parameters taken from the group of parameters consisting of $F_{mos}$ and $\tau_S$.

20. The method of claim 17, wherein step (2) comprises developing a frequency distribution of exactly one of the parameters.

21. Apparatus for in vivo detection of cataractogenesis in ocular tissue of an individual subject, comprising:
  means for analyzing subjects, including, for each subject:
    a light source producing substantially monochromatic, coherent, collimated light;
    optics directing the light to impinge on the subject's ocular tissue;
    a light collector collecting light that is scattered from the subject's ocular tissue; and
    analysis means for performing a correlation analysis on the collected light to determine a signature of cataractogenesis, the signature including a dimensionless parameter $F_{mos}$ and a diffusion decay time parameter ($\tau_S$), where $F_{mos}$ is a measure of the proportion of an intensity of the light scattered by particles in the ocular tissue that move slowly relative to a diffusion speed of other particles in the ocular tissue and $\tau_S$ is a diffusion decay time of the particles that move slowly relative to the diffusion speed of the other particles in the ocular tissue;
  means for developing a frequency distribution of at least one of the parameters; and
  means for determining a rate of cataractogenesis for an individual subject, by comparing the value of at least one parameter of the individual subject to the frequency distribution for the parameter.

22. The apparatus of claim 21, wherein said means for developing a frequency distribution develops a frequency distribution of exactly one of the parameters taken from the group of parameters comprising $F_{mos}$ and $\tau_S$.

23. The apparatus of claim 22, wherein said means for developing a frequency distribution develops a frequency distribution of exactly two of the parameters taken from the group of parameters consisting of $F_{mos}$ and $\tau_S$.

24. The apparatus of claim 21, wherein said means for developing a frequency distribution develops a frequency distribution of exactly one of the parameters.

25. A method for in vivo detection of cataractogenesis in ocular tissue of an individual subject, comprising the steps of:
  (1) For the individual subject, at a first time:
    (a) producing a substantially monochromatic, coherent, collimated light;
    (b) causing the light to impinge on the ocular tissue of the individual subject;
    (c) collecting light that is scattered from the ocular tissue of the individual subject; and
    (d) performing a correlation analysis on the collected light to determine a signature of cataractogenesis, the signature including a dimensionless parameter $F_{mos}$ and a diffusion decay time parameter ($\tau_S$), where $F_{mos}$ is a measure of the proportion of an intensity of the light scattered by particles in the ocular tissue that move slowly relative to a diffusion speed of other particles in the ocular tissue and $\tau_S$ is a diffusion decay time of the particles that move slowly relative to the diffusion speed of the other particles in the ocular tissue;
  (2) for the individual subject, at a second time following the first time:
    (a) producing a substantially monochromatic, coherent, collimated light;
    (b) causing the light to impinge on the ocular tissue of the individual subject;
    (c) collecting light that is scattered from the ocular tissue of the individual subject; and
    (d) performing a correlation analysis on the collected light to determine a signature of cataractogenesis, the signature including a dimensionless parameter $F_{mos}$ and a diffusion decay time parameter ($\tau_S$), where $F_{mos}$ is a measure of the proportion of an intensity of the light scattered by particles in the ocular tissue that move slowly relative to a diffusion speed of other particles in the ocular tissue and $\tau_S$ is a diffusion decay time of the particles that move slowly relative to the diffusion speed of the other particles in the ocular tissue;
  (3) determining a rate of change of at least one of the variables of the individual subject's ocular tissue as a function of age by comparing the at least one variable determined at said first time with the at least one variable determined at said second time;
  (4) for each individual in a population of individuals, at a third time:
    (a) producing a substantially monochromatic, coherent, collimated light;
    (b) causing the light to impinge on the ocular tissue of each individual subject;
    (c) collecting light that is scattered from the ocular tissue of each individual subject; and
    (d) performing a correlation analysis on the collected light to determine a signature of cataractogenesis, the signature including a dimensionless parameter $F_{mos}$ and a diffusion decay time parameter ($\tau_S$), where $F_{mos}$ is a measure of the proportion of an intensity of the light scattered by particles in the ocular tissue that move slowly relative to a diffusion speed of other particles in the ocular tissue and $\tau_S$ is a diffusion decay time of the particles that move slowly relative to the diffusion speed of the other particles in the ocular tissue; and
  (5) comparing the rate of change with individual age of the at least one variable for the particular individual subject to a normal value of the rate of change with age of the at least one variable for the population of subjects by comparing the rate of change of the at least one variable determined at said second time with the at least one variable determined at said third time to detect cataractogenesis in the ocular tissue of the individual subject.

26. Apparatus for in vivo detection of cataractogenesis in ocular tissue of an individual subject, comprising:
  means for analyzing the ocular tissue of the individual subject, at a first time, for analyzing the ocular tissue of the individual subject at a second time following said first time, and for analyzing the ocular tissue of each individual in a population of individuals at a third time, including:
    a light source for producing substantially monochromatic, coherent, collimated light;
    optics for directing the light to impinge on the ocular tissue of the individual subject and the individual in the population of individuals;
    a light collector for collecting light that is scattered from the ocular tissue of the individual subject and the individual in the population of individuals;
    electrical circuitry for performing a correlation analysis on the collected light to determine a signature of cataractogenesis, the signature including a dimensionless parameter $F_{mos}$ and a diffusion decay time parameter ($\tau_S$), where $F_{mos}$ is a measure of the proportion of an intensity of the light scattered by particles in the ocular tissue that move slowly relative to a diffusion speed of other particles in the ocular tissue and $\tau_S$ is a diffusion decay time of the particles that move slowly relative to the diffusion speed of the other particles in the ocular tissue;
  means for determining a rate of change of at least one of the variables of the individual subject's ocular tissue as a function of age; and
  means for comparing the rate of change of the at least one variable for the particular individual subject to a normal value of the rate of change with age of the at least one variable for the population of subjects to detect cataractogenesis in the ocular tissue of the individual subject.

27. A method for in vivo detection of cataractogenesis in ocular tissue, comprising the steps of:
  (a) producing a substantially monochromatic, coherent, collimated light;
  (b) causing the light to impinge on the ocular tissue;
  (c) collecting light that is scattered from the ocular tissue for a predetermined period of time, the scattered light having a fluctuating intensity;

(d) performing a mathematical analysis on the intensity and the fluctuations of the intensity of the collected light, thereby determining a signature of cataractogenesis, the signature including an intensity ($I_{movs}$) of the light scattered by particles in the ocular tissue that move very slowly relative to said predetermined period of time; and (e) determining from the signature the degree of cataractogenesis.

28. The method of claim 27 wherein step (d) comprises computing a temporal autocorrelation function of the fluctuations of the intensity of the collected light.

29. Apparatus for in vivo detection of cataractogenesis in ocular tissue, comprising:

a light source producing a substantially monochromatic, coherent, collimated light;

optics directing the light to impinge on the ocular tissue;

a light collector for collecting light that is scattered from the ocular tissue for a predetermined period of time, the scattered light having a fluctuating intensity;

analysis means for performing a mathematical analysis on the intensity and the fluctuations of the intensity of the collected light, thereby determining a signature of cataractogenesis, the signature including an intensity ($I_{movs}$) of the light scattered by particles in the ocular tissue that move very slowly relative to said predetermined period of time; and means for determining from the signature the degree of cataractogenesis.

30. The apparatus of claim 29 wherein said analysis means computes a temporal autocorrelation function of the fluctuations of the intensity of the collected light.

31. A method for in vivo detection of cataractogenesis in ocular tissue, comprising the steps of:

(a) producing a substantially monochromatic, coherent, collimated light;

(b) causing the light to impinge on the ocular tissue;

(c) collecting light that is scattered from the ocular tissue;

(d) performing a correlation analysis on the collected light to determine a signature of cataractogenesis, the signature including an intensity ($I_{mof}$) of the light scattered by fast moving particles, a diffusion decay time ($\tau_f$) of fast moving particles, an intensity ($I_{mos}$) of the light scattered by slow moving particles, a diffusion decay time ($\tau_S$) of slow moving particles, and an intensity ($I_{movs}$) of the light scattered by particles in the ocular tissue that move very slowly relative to a diffusion speed of other particles in the ocular tissue; and (e) determining from the signature the degree of cataractogenesis.

32. The method of claim 31 wherein step (d) comprises computing a temporal autocorrelation function of the collected light.

33. The method of claim 32 wherein step (d) further comprises performing a least squares analysis on the temporal autocorrelation function to determine the functional form of the function $C(\tau)$ which best fits the temporal autocorrelation function, where $$C(\tau) = a_0[I_{mof}exp(-\tau/\tau_f) + I_{mos}exp(-\tau/\tau_S)]^2 + [I_{mof}+I_{mos}+I_{movs}]^2,$$

$\tau$ is a time delay variable, and $a_0$ is a predetermined constant representative of scattering in the absence of particles in the ocular tissue that move very slowly relative to the diffusion speed of other particles in the ocular tissue.

34. The method of claim 33, further comprising the step of:

(f) determining the value of $a_0$ from in vitro experimentation in the absence of particles in the ocular tissue that move very slowly relative to the diffusion speed of other particles in the ocular tissue.

35. The method of claim 34 wherein step (f) comprises making correlation measurements on a solution of polystyrene spheres.

36. The method of claim 34 wherein step (f) comprises making correlation measurements on a solution of material isolated from an ocular lens containing substantially no particles that move very slowly relative to the diffusion speed of other particles in the tissue.

37. The method of claim 33, further comprising the step of:

(f) making measurements of the value of a parameter representative of light scattering from the ocular lens of each member of a population of individuals and choosing a value of $a_0$ to be the maximum of the measured values.

38. Apparatus for in vivo detection of cataractogenesis in ocular tissue, comprising:

a light source producing substantially monochromatic, coherent, collimated light;

optics directing the light to impinge on the ocular tissue;

a light collector collecting light that is scattered from the ocular tissue;

analysis means for performing a correlation analysis on the collected light to determine a signature of cataractogenesis, the signature including an intensity ($I_{mof}$) of the light scattered by fast moving particles, a diffusion decay time ($\tau_f$) of fast moving particles, an intensity ($I_{mos}$) of the light scattered by slow moving particles, a diffusion decay time ($\tau_S$) of slow moving particles, and an intensity ($I_{movs}$) of the light scattered by particles in the ocular tissue that move very slowly relative to a diffusion speed of the other particles in the ocular tissue; and means for determining from the signature the degree of cataractogenesis.

39. The apparatus of claim 38 wherein said analysis means comprises a computer programmed to compute a temporal autocorrelation function of the intensity of the collected light.

40. The apparatus of claim 38 wherein said analysis means comprises an integrated circuit for computing a temporal autocorrelation function of the intensity of the collected light.

41. The apparatus of claim 38 wherein said analysis means comprises a standalone autocorrelator for computing a temporal autocorrelation function of the intensity of the collected light.

42. The apparatus of claim 38 wherein said analysis means comprises means for performing a least squares analysis on the temporal autocorrelation function to determine the functional form of the function $C(\tau)$ which best fits the temporal autocorrelation function, where $$C(\tau) = a_0[I_{mof}exp(-\tau/\tau_f) + I_{mos}exp(-\tau/\tau_S)]^2 + [I_{mof}+I_{mos}+I_{movs}]^2,$$

τ is a time delay variable, and $\alpha_0$ is a predetermined constant representative of scattering in the absence of particles in the ocular tissue that move very slowly relative to the diffusion speed of other particles in the ocular tissue.

43. The apparatus of claim 42, further comprising means for determining the value of $\alpha_0$ from in vitro experimentation in the absence of particles in the ocular tissue that move very slowly relative to the diffusion speed of the other particles in the ocular tissue.

44. The apparatus of claim 43 wherein the means for determining the value of $\alpha_0$ comprises means for making correlation measurements on a solution of polystyrene spheres.

45. The apparatus of claim 43 wherein the means for determining the value of $\alpha_0$ comprises means for making correlation measurements on a solution of material isolated from an ocular lens containing substantially no particles that move very slowly relative to the diffusion speed of other particles in the tissue.

46. The apparatus of claim 42 wherein said analysis means includes means for making measurements of the value of a parameter representative of light scattering from the ocular lens of each member of a population of individuals and for choosing a value of $\alpha_0$ to be the maximum of the measured values.

47. A method for in vivo detection of cataractogenesis in ocular tissue of an individual subject, comprising the steps of:
(1) For each subject in a population of subjects:
  (a) producing a substantially monochromatic, coherent, collimated light;
  (b) causing the light to impinge on subject's ocular tissue;
  (c) collecting light that is scattered from the ocular tissue; and
  (d) performing a correlation analysis on the collected light to determine values of variables which include an intensity ($I_{mos}$) of the light scattered by slow moving particles, a diffusion decay time ($\tau_S$) of the slow moving particles, and an intensity ($I_{movs}$) of the light scattered by particles in the ocular tissue that move very slowly relative to a diffusion speed of the other particles in the ocular tissue;
(2) developing a frequency distribution of at least one of the variables;
(3) for the individual subject:
  (a) producing a substantially monochromatic, coherent, collimated light;
  (b) causing the light to impinge on the individual subject's ocular tissue;
  (c) collecting light that is scattered from the individual subject's ocular tissue; and
  (d) performing a correlation analysis on the collected light to determine values of variables which include an intensity ($I_{mos}$) of the light scattered by slow moving particles, a diffusion decay time ($\tau_S$) of the slow moving particles, and an intensity ($I_{movs}$) of the light scattered by particles in the ocular tissue that move very slowly relative to a diffusion speed of the other particles in the ocular tissue; and
(4) determining a rate of cataractogenesis for the individual subject, based on the position of the value of at least one variable for the individual subject relative to the frequency distribution for that variable.

48. The method of claim 47, wherein step (2) comprises developing a frequency distribution of two or more of the variables.

49. The method of claim 48, wherein step (2) comprises developing a frequency distribution of exactly two of the variables taken from the group of variables consisting of $I_{mos}$, $\tau_S$, and $I_{movs}$.

50. The method of claim 47, wherein step (2) comprises developing a frequency distribution of exactly one of the variables.

51. Apparatus for in vivo detection of cataractogenesis in ocular tissue of an individual subject, comprising:
means for analyzing the individual subject and subjects in a population, including, for each subject:
  a light source producing substantially monochromatic, coherent, collimated light;
  optics directing the light to impinge on the subject's ocular tissue;
  a light collector collecting light that is scattered from the subject's ocular tissue;
  analysis means for performing a correlation analysis on the collected light to determine values of variables, including an intensity ($I_{mos}$) of the light scattered by slow moving particles, a diffusion decay time ($\tau_S$) of the slow moving particles in the subject's ocular tissue, and an intensity ($I_{movs}$) of the light scattered by particles in the ocular tissue that move very slowly relative to a diffusion speed of the other particles in the ocular tissue;
means for developing a frequency distribution of at least one of the variables and from the values of variables for the population of subjects; and
means for determining a rage of cataractogenesis for the individual subject by comparing the value of at least one variable for the individual subject to the frequency distribution for the variable.

52. The apparatus of claim 51, wherein said means for developing a frequency distribution develops a frequency distribution of two or more of the variables.

53. The apparatus of claim 52, wherein said means for developing a frequency distribution develops a frequency distribution of exactly two of the variables taken from the group of variables consisting of $I_{mos}$, $\tau_S$, and $I_{movs}$.

54. The apparatus of claim 51, wherein said means for developing a frequency distribution develops a frequency distribution of exactly one of the variables.

55. The method for in vivo detection of cataractogenesis in ocular tissue of an individual subject, comprising the steps of:
(1) For the individual subject, at a first time:
  (a) producing a substantially monochromatic, coherent, collimated light;
  (b) causing the light to impinge on the ocular tissue of the individual subject;
  (c) collecting light that is scattered from the ocular tissue of the individual subject over a predetermined first time period; and
  (d) performing a correlation analysis on the collected light to determine values of variables, including an intensity ($I_{mos}$) of the light scattered by slow moving particles in the individual subject's ocular tissue, a diffusion decay time ($\tau_S$) of the slow moving particles in the individual subject's ocular tissue, and an intensity ($I_{movs}$) of the light scattered by particles in the ocular tissue that move very slowly relative to the first time period over which the light is collected in the individual subject's ocular tissue;

(2) for the individual subject, at a second time following the first time:

(a) producing a substantially monochromatic, coherent, collimated light;

(b) causing the light to impinge on the ocular tissue of the individual subject;

(c) collecting light that is scattered form the ocular tissue of the individual subject over a predetermined second time period; and (d) performing a correlation analysis on the collected light to determine values of variables, including an intensity ($I_{mos}$) of the light scattered by slow moving particles in the individual subject's ocular tissue, a diffusion decay time ($\tau_S$) of the slow moving particles in the individual subject's ocular tissue, and an intensity ($I_{movs}$) of the light scattered by particles in the ocular tissue that move very slowly relative to the second time period over which the light is collected in the ocular tissue;

(3) determining a rate of change of at least one of the variables of the individual subject's ocular tissue as a function of age;

(4) for each individual in a population of individuals, at a third time:

(a) producing a substantially monochromatic, coherent, collimated light;

(b) causing the light to impinge on the ocular tissue of each individual in the population of individuals;

(c) collecting light that is scattered from the ocular tissue of each individual in the population of individuals over a predetermined third time period; and (d) performing a correlation analysis on the collected light to determine normal values of the rate of change with individual age of the variables for the population, including an intensity ($I_{mos}$) of the light scattered by slow moving particles within the ocular tissue of individuals in the population of individuals, a diffusion decay time ($\tau_S$) of the slow moving particles in the subject's ocular tissue, and an intensity ($I_{movs}$) of the light scattered by particles in the ocular tissue that move very slowly relative to the their time period over which the light is collected in the ocular tissue; and (5) comparing the rate of change with individual age of the at least one variable for the particular individual subject to the normal value of the rate of change with age of the at least one variable for the population of subjects to detect cataractogenesis in the ocular tissue of the individual subject.

56. Apparatus for in vivo detection of cataractogenesis in ocular tissue of an individual subject, comprising:

means for analyzing the ocular tissue of the individual subject at a first time, for analyzing the ocular tissue of the individual subject at a second time following the first time and for analyzing the ocular tissue of each individual in a population of individuals at a third time including:

a light source for producing substantially monochromatic, coherent, collimated light;

optics for directing the light to impinge on the ocular tissue of the individual subject and individuals in the population;

a light collector for collecting light that is scattered from the ocular tissue of the individual subject over a predetermined first time period; and electrical circuitry for performing a correlation analysis on the collected light to determine the values of variables, including the intensity ($I_{mos}$) of the light scattered by slow moving particles, the diffusion decay time ($\tau_S$) of the slow moving particles, and the intensity ($I_{movs}$) of the light scattered by particles in the ocular tissue that move very slowly relative to the first time period over which the light is collected in the ocular tissue of the subject;

means for analyzing the ocular tissue of the individual subject at a second time following the first time, including:

a light source for producing substantially monochromatic, coherent, collimated light;

optics for directing the light to impinge on the ocular tissue of the individual subject;

a light collector for collecting light that is scattered from the ocular tissue of the individual subject over a predetermined second time period; and electrical circuitry for performing a correlation analysis on the collected light to determine the values of variables, including the intensity ($I_{mos}$) of the light scattered by slow moving particles, the diffusion decay time ($\tau_S$) of the slow moving particles, and the intensity ($I_{movs}$) of the light scattered by particles in the ocular tissue that move very slowly relative to the second time period over which the light is collected in the ocular tissue of the subject;

apparatus for determining the rate of change of at least one of the variables o the individual subject's ocular tissue as a function of age;

means for analyzing the ocular tissue of each individual in a population of individuals at a third time, including:

a light source for producing substantially monochromatic, coherent, collimated light;

optics for directing the light to impinge on the ocular tissue of each individual subject;

a light collector for collecting light that is scattered from the ocular tissue of each individual subject over a predetermined third time period; and electrical circuitry for performing a correlation analysis on the collected light to determine normal values of the variables for the population, including the intensity ($I_{mos}$) of the light scattered by slow moving particles, the diffusion decay time ($\tau_S$) of the slow moving particles, and the intensity ($I_{movs}$) of the light scattered by particles in the ocular tissue that move very slowly relative to the third time period over which the light is collected in the ocular tissue of the subject; and electrical circuitry comparing the rate of change of the at least one variable for the particular individual subject to the normal value of the rate of change with age of the at least one variable for the population of subjects to detect cataractogenesis in the ocular tissue of the individual subject.

* * * * *

UNITED STATES PATENT AND TRADEMARK OFFICE
CERTIFICATE OF CORRECTION

PATENT NO. : 5,392,776
DATED : February 28, 1995
INVENTOR(S) : George M. Thurston et al.

It is certified that error appears in the above-identified patent and that said Letters Patent is hereby corrected as shown below:

In column 14, claim 3, line 18, please delete "]" and substitute therefor --[--.

In column 14, claim 3, line 20, please delete "r" and substitute therefor --$T$--.

In column 15, claim 10, line 13, please delete "]" and substitute therefor --[--.

Signed and Sealed this

Twenty-ninth Day of August, 1995

Attest:

BRUCE LEHMAN

Attesting Officer            Commissioner of Patents and Trademarks

UNITED STATES PATENT AND TRADEMARK OFFICE
CERTIFICATE OF CORRECTION

PATENT NO.    : 5,392,776
DATED         : February 28, 1995
INVENTOR(S)   : George M. Thurston et al.

It is certified that error appears in the above identified patent and that said Letters Patent is hereby corrected as shown below:

In column 1, following the title and before the heading "TECHNICAL FIELD", please insert the following acknowledgement:

--This invention was made with government support under Grant No. NIH-5R01-EY05127 by the National Institutes of Health. The government has certain rights in the invention.--

Signed and Sealed this

Twenty-sixth Day of March, 1996

Attest:

BRUCE LEHMAN

Attesting Officer

Commissioner of Patents and Trademarks